US011466122B2

(12) United States Patent
Srivastava et al.

(10) Patent No.: US 11,466,122 B2
(45) Date of Patent: Oct. 11, 2022

(54) POLYETHYLENEIMINE COMPOUNDS CONTAINING N-HALAMINE AND DERIVATIVES THEREOF

(71) Applicant: Milliken & Company, Spartanburg, SC (US)

(72) Inventors: Sudhanshu Srivastava, Greer, SC (US); Wesley A. Freund, Simpsonville, SC (US); Sanjeev K. Dey, Spartanburg, SC (US); Dominick J. Valenti, Moore, SC (US)

( * ) Notice: Subject to any disclaimer, the term of this patent is extended or adjusted under 35 U.S.C. 154(b) by 574 days.

(21) Appl. No.: 16/590,649

(22) Filed: Oct. 2, 2019

(65) Prior Publication Data
US 2020/0123320 A1 Apr. 23, 2020

Related U.S. Application Data

(60) Provisional application No. 62/747,174, filed on Oct. 18, 2018.

(51) Int. Cl.
| | | |
|---|---|---|
| C11D 3/37 | (2006.01) |
| C08G 73/02 | (2006.01) |
| A61L 2/232 | (2006.01) |
| C09D 179/02 | (2006.01) |
| C11D 3/00 | (2006.01) |
| D06M 13/00 | (2006.01) |

(52) U.S. Cl.
CPC .......... *C08G 73/0206* (2013.01); *A61L 2/232* (2013.01); *C09D 179/02* (2013.01); *C11D 3/0068* (2013.01); *C11D 3/3723* (2013.01); *D06M 13/005* (2013.01)

(58) Field of Classification Search
CPC .................................................. C11D 3/3723
See application file for complete search history.

(56) References Cited

U.S. PATENT DOCUMENTS

| | | | |
|---|---|---|---|
| 2,272,489 A | 2/1942 | Ulrich et al. ................. 260/239 |
| 2,381,020 A | 8/1945 | Wilkes et al. ................. 8/142.5 |
| 2,472,361 A | 6/1949 | Arsem .......................... 260/583 |
| 3,262,791 A | 7/1966 | Dickson et al. ................ 106/14 |
| 3,301,783 A | 1/1967 | Dickson et al. ............ 252/47.5 |
| 3,425,549 A | 2/1969 | Dickson et al. ............. 209/166 |
| 3,622,528 A | 11/1971 | Longoria, III et al. ......... 260/18 |
| 3,639,290 A | 2/1972 | Fearnley |
| 3,844,952 A | 10/1974 | Booth .......................... 252/8.75 |
| 4,532,187 A | 7/1985 | Hoenig |
| 4,846,846 A | 7/1989 | Rekers et al. ..................... 8/515 |
| 5,082,938 A | 1/1992 | Kluger et al. ................... 544/38 |
| 5,135,972 A | 8/1992 | Kluger et al. ................... 524/88 |
| 5,217,813 A | 6/1993 | Roser |
| 5,460,736 A | 10/1995 | Trinh et al. ..................... 252/8.8 |
| 5,591,833 A | 1/1997 | Hines et al. .................. 534/607 |
| 5,733,272 A | 3/1998 | Brunner et al. .............. 604/359 |
| 5,968,404 A | 10/1999 | Trinh et al. .................. 252/8.91 |
| 6,046,155 A | 4/2000 | Trinh et al. ................... 510/516 |
| 6,127,331 A | 10/2000 | Cleary et al. ................. 510/528 |
| 6,147,045 A | 11/2000 | Lappas .......................... 510/305 |
| 6,593,483 B2 | 7/2003 | Xia ............................... 552/259 |
| 6,726,936 B1 | 4/2004 | Asano et al. ................. 424/618 |
| 7,141,077 B2 | 11/2006 | Detering et al. .................. 8/137 |
| 7,754,197 B2 | 7/2010 | Wu et al. ..................... 424/76.2 |
| 9,260,817 B2 | 2/2016 | Williams et al. ............. 424/400 |
| 9,273,427 B2 | 3/2016 | Williams et al. ............. 424/400 |
| 11,299,591 B2 | 4/2022 | Srivastava |
| 2003/0194504 A1 | 10/2003 | Bilyk |
| 2003/0215417 A1 | 11/2003 | Uchiyama et al. .......... 424/76.2 |
| 2004/0198851 A1 | 10/2004 | Becker |
| 2005/0084474 A1 | 4/2005 | Wu et al. ..................... 424/76.1 |
| 2005/0183207 A1 | 8/2005 | Chan |
| 2007/0028394 A1 | 2/2007 | Durrant |
| 2007/0231291 A1 | 10/2007 | Huang |
| 2008/0163437 A1 | 7/2008 | Fang et al. ........................ 8/442 |
| 2008/0164439 A1 | 7/2008 | Fang et al. ................... 252/8.61 |
| 2009/0246258 A1 | 10/2009 | Shukla et al. ................ 424/443 |
| 2012/0183488 A1 | 7/2012 | Woo et al. ................... 424/76.1 |
| 2014/0349913 A1* | 11/2014 | Delaney .................... C11D 3/30 510/488 |
| 2015/0093351 A1 | 4/2015 | Horenziak ................... 424/76.1 |
| 2015/0098922 A1 | 4/2015 | Madhav et al. |
| 2015/0099689 A1 | 4/2015 | Madhav et al. |
| 2015/0104856 A1 | 4/2015 | Astrid |
| 2015/0203799 A1 | 7/2015 | Bettiol |
| 2015/0336338 A1 | 11/2015 | Bordere |
| 2015/0353869 A1 | 12/2015 | Stenger |
| 2016/0090555 A1 | 3/2016 | Frankenbach |
| 2017/0081618 A1 | 3/2017 | Gohl |

(Continued)

FOREIGN PATENT DOCUMENTS

| | | |
|---|---|---|
| CA | 1173631 | 9/1984 |
| EP | 2100906 | 9/2009 |
| EP | 3202265 | 8/2017 |

(Continued)

OTHER PUBLICATIONS

Patent Cooperation Treaty PCT International Search Report. dated Dec. 16, 2019. International Application No. PCT/US2019/055244. International Filing Date: Oct. 8, 2019.
Gang Sun., "*Biocidal Halamine Chemistry for Woven and Nonwoven Textiles*". Division of Textiles and Clothing, University of California, Davis.
Hao Liu et al., "*Double-layered Hyaluronic Acid/stearic Acid-modified Polyethyleneimine Nanoparticles Encapsulating (-)-gossypol: a Nanocarrier for Chiral Anticancer drugs*". J Mater Chem B Mater Biol Med. Aug. 28, 2014; 2(32): 5238-5248.
Aws Alshamsan et al., "*Formulation and Deliver of sIRNA by Oleic Acid and Stearic Acid Modified Polyethylenimine*". Mol. Phamaceutics, 2009, 6 (1), pp. 121-135, Publication Date (Web) Dec. 2, 2008.
Agustin S. Picco et al., "*Probing the Microenvironment of Unimicelles Constituted of Amphiphilic Hyperbranched Polyethyleneimine Using 1-methyl-8-Oxyquinolinium Betaine*"., www.rsc.org/pccp.

(Continued)

Primary Examiner — Gregory E Webb
(74) Attorney, Agent, or Firm — Brenda D. Wentz

(57) ABSTRACT

This invention relates to odor control molecules comprised of polyethyleneimine compounds containing N-halamine and derivatives thereof.

22 Claims, No Drawings

(56) References Cited

U.S. PATENT DOCUMENTS

| | | |
|---|---|---|
| 2018/0265808 A1 | 9/2018 | Gross |
| 2018/0362714 A1 | 12/2018 | Grubbs |

FOREIGN PATENT DOCUMENTS

| | | |
|---|---|---|
| EP | 3434706 | 1/2019 |
| WO | WO 98/20098 | 5/1998 |
| WO | WO 98/26808 | 6/1998 |
| WO | WO 99/67353 | 12/1999 |
| WO | 2007085552 | 8/2007 |
| WO | WO 2008/085902 | 7/2008 |
| WO | WO 2008/156636 | 12/2008 |
| WO | WO 2016/049389 | 3/2016 |
| WO | WO 2017/060485 | 4/2017 |
| WO | 2017163863 | 9/2017 |

OTHER PUBLICATIONS

Peter Kovacic et al. "Chemistry of N-Bromamines and N-Chloramines *Tin Compounds Reaction 2. Formation of a-AminoKetones 3. Via Nitrenium Ion and Miscellaneous Types F", Jan. 1, 1968 (Jan. 1, 1968, XP055659551, retrieved from the Internet: URL: https://www.thevespiary.org/rhodium/rhodium/Vespiary/talk/files/5533-chloraminereview358b.pdf.

Patent Cooperation Treaty PCT International Search Report. dated Dec. 13, 2019. International Application No. PCT/US2019/055234. International Filing Date: Oct. 8, 2019.

Patent Cooperation Treaty PCT International Search Report. dated Dec. 16, 2019. International Application No. PCT/US2019/055238. International Filing Date: Oct. 8, 2019.

Patent Cooperation Treaty PCT International Search Report. dated Dec. 16, 2019. International Application No. PCT/US2019/055242. International Filing Date: Oct. 8, 2019.

Patent Cooperation Treaty PCT International Search Report. dated Dec. 16, 2019. International Application No. PCT/US2019/055248. International Filing Date: Oct. 8, 2019.

Patent Cooperation Treaty PCT International Search Report. dated Feb. 3, 2020. International Application No. PCT/US2019/055227. International Filing Date: Oct. 8, 2019.

Patent Cooperation Treaty PCT International Search Report. dated Feb. 3, 2020. International Application No. PCT/US2019/055240. International Filing Date: Oct. 8, 2019.

* cited by examiner

US 11,466,122 B2

POLYETHYLENEIMINE COMPOUNDS CONTAINING N-HALAMINE AND DERIVATIVES THEREOF

CROSS REFERENCE TO RELATED APPLICATIONS

This application claims priority to U.S. Provisional Patent Application No. 62/747,174, entitled "Polyethyleneimine Compounds Containing N-Halamine and Derivatives Thereof" which was filed on Oct. 18, 2018, and which is entirely incorporated by reference herein.

TECHNICAL FIELD

This invention relates to odor control molecules comprised of polyethyleneimine compounds containing N-halamine and derivatives thereof.

BACKGROUND

Odor control for textile substrates has been an ongoing area of investigation for decades. This invention focuses, in particular, on odor control for textile substrates comprised of cotton, polyester, and/or polyester/cotton blends, which are designed for use as activewear fabrics. Activewear fabrics are those typically worn for exercise and are often worn on a regular basis. These activewear fabrics are typically exposed to higher levels of body fluids, such as perspiration and sweat, than other types of fabrics. Over time, even with proper washing, unpleasant odor tends to build up on these fabrics and is generally difficult to neutralize by repeated laundering.

As a result, there is a continued need to improve the odor control performance of these types of fabrics. The present invention provides an odor control molecule comprised of a polyethyleneimine composition containing N-halamine and derivatives thereof which has been demonstrated to neutralize the unpleasant odors associated with activewear fabrics. Incorporating this odor control molecule in a laundry care composition provides one possible and successful delivery mechanism for deposition onto a textile substrate. Each time the textile substrates are washed, the odor control molecule is deposited on the textile substrates. Thus, the textile substrates remain smelling fresh for a longer period of time.

BRIEF SUMMARY

In one aspect, the invention relates to a polyethyleneimine compound comprising a plurality of amine groups, each amine group comprising a nitrogen atom, wherein: (a) at least one amine group comprises a nitrogen atom directly bonded to a functional group selected from the group consisting of alkanoyl groups, alkenoyl groups, aroyl groups, alkyl groups containing three or more carbon atoms, and aryl groups; and (b) at least one amine group comprises a nitrogen atom directly bonded to a halogen.

In another aspect, the invention relates to a polyethyleneimine compound comprising a plurality of amine groups, each amine group comprising a nitrogen atom, wherein: (a) at least one amine group comprises a nitrogen atom directly bonded to at least one alkyleneoxy group; and (b) at least one amine group comprises a nitrogen atom directly bonded to a halogen.

In a further aspect, the invention relates to a laundry care composition comprising: (a) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; and (b) at least one laundry care ingredient.

In yet a further aspect, the invention relates to a laundry care composition comprising: (a) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; (b) a polyethyleneimine compound comprising a plurality of amine groups, each amine group comprising a nitrogen atom, wherein: (i) at least one amine group comprises a nitrogen atom directly bonded to at least one alkyleneoxy group, and (ii) at least one amine group comprises a nitrogen atom directly bonded to a halogen; and (c) at least one laundry care ingredient.

In another aspect, the invention relates to a floorcovering cleaning composition comprising: (a) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; and (b) at least one floorcovering cleaning ingredient.

In a further aspect, the invention relates to a floorcovering cleaning composition comprising: (a) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; (b) a polyethyleneimine compound comprising a plurality of amine groups, each amine group comprising a nitrogen atom, wherein: (i) at least one amine group comprises a nitrogen atom directly bonded to at least one alkyleneoxy group, and (ii) at least one amine group comprises a nitrogen atom directly bonded to a halogen; and (c) at least one floorcovering cleaning ingredient.

In another aspect, the invention relates to an article comprising: (a) at least one textile substrate, and (b) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen.

In a further aspect, the invention relates to an article comprising: (a) at least one textile substrate; (b) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; and (c) a polyethyleneimine compound comprising a plurality of amine groups, each amine group comprising a nitrogen atom, wherein: (i) at least one amine group comprises a nitrogen atom directly bonded to at least one alkyleneoxy group, and (ii) at least one amine group comprises a nitrogen atom directly bonded to a halogen.

In yet another aspect, the invention relates to a process for controlling odor on a textile substrate comprising the steps of: (a) providing a textile substrate, and (b) applying to or depositing on the textile substrate a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen.

In another aspect, the invention relates to an odor control molecule formed by reacting a polyethyleneimine molecule with stearic acid in the presence of an aqueous chlorine-containing solution.

In a further aspect, the invention relates to an odor control molecule comprising a halogenated polyethyleneimine, wherein odor control is achieved by proton transfer from at least one volatile carboxylic acid to the halogenated polyethyleneimine.

In another aspect, the invention relates to a process for controlling odor on a textile substrate comprising the steps of: (a) providing a textile substrate, and (b) treating the textile substrate with a compound formed by the reaction of polyethyleneimine with stearic acid in the presence of an aqueous chlorine-containing solution.

In yet a further aspect, the invention relates to an article comprising: (a) at least one thermoset material, and (b) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen.

In another aspect, the invention relates to an article comprising: (a) at least one thermoset material; (b) a polyethyleneimine compound comprising a plurality of amine groups, each amine group comprising a nitrogen atom, wherein: (i) at least one amine group comprises a nitrogen atom directly bonded to a functional group selected from the group consisting of alkanoyl groups, alkenoyl groups, aroyl groups, alkyl groups containing three or more carbon atoms, and aryl groups, and (ii) at least one amine group comprises a nitrogen atom directly bonded to a halogen; and (c) a polyethyleneimine compound comprising a plurality of amine groups, each amine group comprising a nitrogen atom, wherein: (i) at least one amine group comprises a nitrogen atom directly bonded to at least one alkyleneoxy group, and (ii) at least one amine group comprises a nitrogen atom directly bonded to a halogen.

DETAILED DESCRIPTION

The invention described herein is an odor control molecule comprised of a polyethyleneimine composition containing N-halamine and derivatives thereof. In one aspect of the invention, the odor control molecule is added to a textile substrate via a laundry care composition during a standard laundering process. The laundry care composition that contains the odor control molecule is added to a washing machine, thereby allowing the molecule to come into direct contact with the textile substrate. Thus, during the laundry process, the odor control molecule is deposited onto at least one surface of the textile substrate and improvement in odor control is achieved.

As used herein, the term "alkoxy" is intended to include $C_1$-$C_8$ alkoxy and alkoxy derivatives of polyols having repeating units such as butylene oxide, glycidol oxide, ethylene oxide or propylene oxide.

As used herein, unless otherwise specified, the terms "alkyl" and "alkyl capped" are intended to include $C_2$ to $C_{100}$ alkyl groups, $C_2$ to $C_{50}$ alkyl groups, $C_5$-$C_{25}$ alkyl groups, or even $C_{10}$-$C_{20}$ alkyl groups.

As used herein, unless otherwise specified, the term "aryl" is intended to include $C_6$-$C_{12}$ aryl groups.

As used herein, unless otherwise specified, the term "arylalkyl" is intended to include $C_1$-$C_{18}$ alkyl groups and, in one aspect, $C_1$-$C_6$ alkyl groups.

As used herein, unless otherwise specified, the term "alkanoyl" refers to univalent groups of the formula —C(O)$R^a$, where $R^a$ is an alkyl group, preferably a $C_3$-$C_{29}$ alkyl group.

As used herein, unless otherwise specified, the term "alkenyl" refers to univalent groups derived from acyclic olefinic hydrocarbons by removal of a hydrogen atom from any carbon atom. In the context of this definition, the term "acyclic olefinic hydrocarbons" refers to acyclic hydrocarbons containing one or more carbon-carbon double bonds.

A used herein, unless otherwise specified, the term "alkenoyl" refers to univalent groups of the formula —C(O)$R^b$, where $R^b$ is an alkenyl group, preferably a $C_3$-$C_{29}$ alkenyl group.

A used herein, unless otherwise specified, the term "aroyl" refers to univalent groups of the formula —C(O)$R^c$, where $R^c$ is an aryl group, preferably a $C_6$-$C_{10}$ aryl group.

The terms "ethylene oxide," "propylene oxide" and "butylene oxide" may be shown herein by their typical designation of "EO," "PO" and "BO," respectively.

All percentages and ratios are calculated by weight unless otherwise indicated. All percentages and ratios are calculated based on the total composition unless otherwise indicated.

Polyethyleneimine compounds and polyethyleneimine derivatives suitable for use in the present invention may contain various groups, such as the oxyalkylated, acylated, alkylated, carbonylated, olefiniated, and the like, derivatives thereof, prepared by introducing such groups individually, alternatively, and/or in combination, including for example, derivatives prepared by varying the order of adding such groups, by increasing the number and order of adding such groups, and the like.

An exemplary structure of a polyethyleneimine ("PEI") molecule is shown below as Formula P:

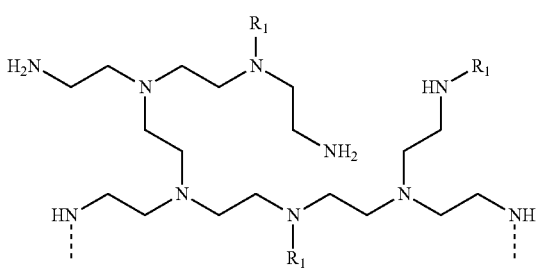

(P)

wherein each $R_1$ is independently selected from the group consisting of hydrogen, alkyl, $C_2$-$C_{18}$ alkanoyl and $C_2$-$C_6$ alkanoyl. In the structure (and in other structures shown throughout the description of the invention), the dashed bonds connected to the nitrogen atoms represent bonds to other portions of the polyethyleneimine molecule. In other words, the dashed bonds represent the continuation of the polyethyleneimine backbone or framework.

Another exemplary structure of a polyethyleneimine ("PEI") molecule is shown below as Formula Q:

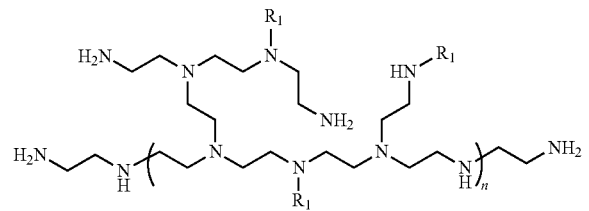

(Q)

wherein each $R_1$ is independently selected from the group consisting of hydrogen, alkyl, $C_2$-$C_{18}$ alkanoyl and $C_2$-$C_6$ alkanoyl; and n is 2 to 100,000.

The average molecular weight ("MW") of PEI is in the range from about 300 to about 2 million, or in the range from about 500 to about 1 million, or in the range from about 800 to about 500,000, or in the range from about 1000 to about 250,000, or in the range from about 1000 to about 100,000, or in the range from about 1000 to about 75,000, or in the range from about 1000 to about 50,000, or in the range from about 1000 to about 30,000. It should be understood that, as a consequence of its manufacturing process, molecular weight is actually reported as "average molecular weight" and is based on a distribution of molecular weights.

The odor control molecule of the present invention includes a polyethyleneimine compound comprising a plurality of amine groups, each amine group comprising a nitrogen atom, wherein:

a. at least one amine group comprises a nitrogen atom directly bonded to a functional group selected from the group consisting of alkanoyl groups, alkenoyl groups, aroyl groups, alkyl groups containing three or more carbon atoms, and aryl groups; and b. at least one amine group comprises a nitrogen atom directly bonded to a halogen.

The functional group may further be selected from the group consisting of $C_{10}$-$C_{26}$ alkanoyl groups, $C_{10}$-$C_{26}$ alkenoyl groups, aroyl groups, $C_{10}$-$C_{26}$ alkyl groups and aryl groups.

In a preferred embodiment, at least one amine group in the substituted polyethyleneimine compound may be characterized by the following Formula (X):

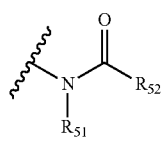

(X)

wherein $R_{51}$ is selected from the group consisting of hydrogen, halogen, and alkylamines, and $R_{52}$ is selected from the group consisting of alkyl groups, alkenyl groups, and aryl groups. $R_{51}$ can be any suitable alkylamine, such as an alkylamine of the formula —$(CH_2CH_2NH)_gH$, where g is an integer equal to or greater than 1. Preferably, $R_{51}$ is hydrogen or halogen. In a preferred embodiment, $R_{52}$ is selected from the group consisting of $C_9$-$C_{25}$ alkyl groups, more preferably $C_9$-$C_{19}$ alkyl groups or $C_9$-$C_{17}$ alkyl groups. In the structure of Formulae (X) and (Z) and those that follow, the bond truncated by the wavy line represents a bond to an adjacent portion of the polyethyleneimine structure.

In a preferred embodiment, at least one amine group in the substituted polyethyleneimine compound may be characterized by the following Formula (Y):

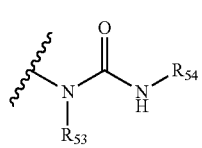

(Y)

wherein $R_{53}$ is selected from the group consisting of hydrogen, halogen, and alkylamines, and $R_{54}$ is selected from the group consisting of alkyl groups, alkenyl groups, and aryl groups. $R_{53}$ can be any suitable alkylamine, such as an alkylamine of the formula —$(CH_2CH_2NH)_gH$, where g is an integer equal to or greater than 1. Preferably, $R_{53}$ is hydrogen or halogen. In a preferred embodiment, $R_{54}$ is selected from the group consisting of $C_9$-$C_{25}$ alkyl groups, more preferably $C_9$-$C_{19}$ alkyl groups or $C_9$-$C_{17}$ alkyl groups.

In a preferred embodiment, at least one amine group in the substituted polyethyleneimine compound may be characterized by the following Formula (Z):

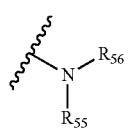

(Z)

wherein $R_{55}$ is selected from the group consisting of hydrogen, halogen, and alkylamines, and $R_{56}$ is selected from the group consisting of alkyl groups (e.g., alkyl groups having three or more carbon atoms), alkenyl groups, and aryl groups. $R_{55}$ can be any suitable alkylamine, such as an alkylamine of the formula —$(CH_2CH_2NH)_gH$, where g is an integer equal to or greater than 1. Preferably, $R_{55}$ is hydrogen or halogen. In a preferred embodiment, $R_{56}$ is selected from the group consisting of $C_9$-$C_{26}$ alkyl groups, more preferably $C_9$-$C_{19}$ alkyl groups or $C_9$-$C_{17}$ alkyl groups. In another preferred embodiment, $R_{56}$ is selected from the group consisting of aryl groups, with a phenyl group being particularly preferred.

In another preferred embodiment, at least one amine group in the substituted polyethyleneimine compound may be characterized by the following Formula (H):

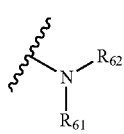

(H)

wherein $R_{61}$ is selected from the group consisting of hydrogen, halogen, and alkylamines, and $R_{62}$ is a halogen. In Formula (H), $R_{61}$ is selected from the group consisting of hydrogen, halogen, and alkylamines, including the same alkylamines described above for $R_{51}$ from Formula (X). Preferably, $R_{61}$ is hydrogen or halogen. In a preferred embodiment, $R_{62}$ is selected from the group consisting of chlorine, bromine, fluorine, and iodine, with chlorine being particularly preferred.

In a further aspect of the invention, the odor control molecule may include at least one amine group of Formula (X), (Y), or (Z) and at least one amine group of Formula (H).

In another embodiment, the invention provides a polyethylenimine compound that is substituted with an alkyleneoxy group and a halamine group. In particular, the invention provides a polyethyleneimine compound comprising a plurality of amine groups, each amine group comprising a nitrogen atom, wherein: (a) at least one amine group comprises a nitrogen atom directly bonded to at least one alkyleneoxy group; and (b) at least one amine group comprises a nitrogen atom directly bonded to a halogen.

In such a polyethylenimine compound, the amine group comprising a nitrogen atom directly bonded to at least one alkyleneoxy group can conform to Formula (J):

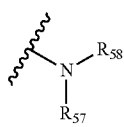

(J)

wherein $R_{57}$ is selected from the group consisting of hydrogen, halogen, alkyleneoxy, and alkylamines, and $R_{58}$ is alkyleneoxy. $R_{57}$ can be any suitable alkylamine, such as an alkylamine of the formula —(CH$_2$CH$_2$NH)$_g$H, where g is an integer equal to or greater than 1. Preferably, $R_{57}$ is hydrogen, halogen, or alkyleneoxy.

In such an embodiment, the polyethylenimine compound can comprise any suitable alkyleneoxy group. Suitable alkyleneoxy groups include those of Formula (C) below:

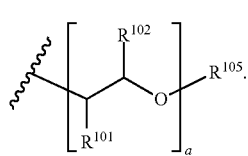

(C)

In the structure of Formula (C) and the other alkyleneoxy structures that follow, the carbon atom bonded to $R^{101}$ is also bonded to the nitrogen atom of the amine group. In the structure of Formula (C), each $R^{101}$ and $R^{102}$ group is independently selected from the group consisting of hydrogen, alkyl, aryl, alkoxyalkyl, and aryloxyalkyl. $R^{105}$ is a terminal group for the oxyalkylene and can be selected from the group consisting of hydrogen, alkyl groups (e.g., $C_1$-$C_4$ alkyl groups), and aryl groups, with hydrogen being preferred. Preferably, each $R^{101}$ and $R^{102}$ group is independently selected from the group consisting of hydrogen and alkyl (e.g., $C_1$-$C_4$ alkyl). The variable a is an integer equal to or greater than 1 (e.g., from 1 to about 100). For each monomer unit in the alkyleneoxy group, the $R^{101}$ and $R^{102}$ groups are independently selected from the recited group. Thus, when the variable a is greater than 1, the alkyleneoxy group can be comprised of two or more monomer units covalently bonded to form the alkyleneoxy group, or even three or more monomer units. When the alkyleneoxy group comprises two or more monomer units (or even three or more monomer units), these monomer units can be arranged in either a block configuration or in a random configuration, but a block configuration generally is more preferred. In a preferred embodiment, the alkyleneoxy group comprises monomer units independently selected from the group consisting of ethyleneoxy, propyleneoxy, and butyleneoxy. A suitable example of such an alkyleneoxy group is Formula (CI) below:

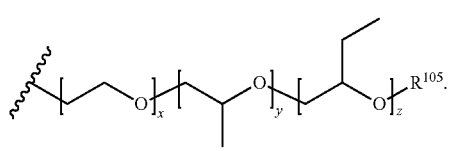

(CI)

In the structure of Formula (CI), the variables x, y, and z are independently selected from the group consisting of zero and positive integers (e.g., positive integers from 1 to about 100). Preferably, the sum of x, y, and z is 2 or more or 3 or more (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). $R^{105}$ is a terminal group for the oxyalkylene and can be selected from the group consisting of hydrogen, alkyl groups (e.g., $C_1$-$C_4$ alkyl groups), and aryl groups, with hydrogen being preferred. In certain possibly preferred embodiments, the alkyleneoxy group comprises ethyleneoxy and propyleneoxy monomer units arranged in a block configuration. Suitable examples of such alkyleneoxy groups include those of Formulae (CII) and (CIII) below

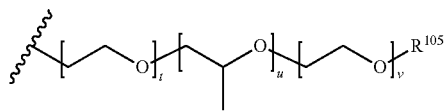

(CII)

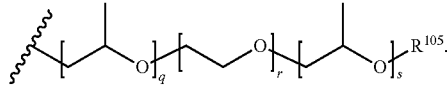

(CIII)

In the structures of Formulae (CII) and (CIII), the variables, t, u, v, q, r, and s are independently selected from the group consisting of zero and positive integers (e.g., positive integers from 1 to about 100). Preferably, the sum of t, u, and v and q, r, and s is 2 or more or 3 or more (e.g., 2 to about 300, 3 to about 300, 2 to about 200, 3 to about 200, 2 to about 100, 3 to about 100, 2 to about 50, 3 to about 50, 2 to about 30, 3 to about 30, 2 to about 25, 3 to about 25, 2 to about 20, 3 to about 20, 2 to about 15, 3 to about 15, 2 to about 10, or 3 to about 10). $R^{105}$ is a terminal group for the oxyalkylene and can be selected from the group consisting of hydrogen, alkyl groups (e.g., $C_1$-$C_4$ alkyl groups), and aryl groups, with hydrogen being preferred.

The odor control molecule is formed by reacting an electrophilic compound with polyethyleneimine in the presence of at least one halogen-containing composition. The resulting substituted polyethyleneimine compound contains at least one halogen atom. The substituted polyethyleneimine compound has a molecular weight in the range from about 400 to about 50,000, or in the range from about 600 to about 30,000, or even in the range from about 600 to about 15,000. The substituted polyethyleneimine compound has been demonstrated to provide improved odor control on textiles substrates treated therewith.

In the general reaction scheme, the electrophilic compound (such as stearic acid) reacts with at least one nitrogen atom on the PEI molecule to form a new group on an amine group of the PEI, in the general reaction scheme a new amide group is formed through the reaction with stearic acid. The ratio of PEI to the electrophilic compound, based on molecular weight of the PEI molecule, may be tailored to make the substituted polyethyleneimine compound sufficiently hydrophobic so that it will deposit on the textile substrate (e.g. fabric) during the laundering process. The substituted polyethyleneimine compound may be formed by adding halogen-containing liquid (e.g. water containing a halogen source) to the PEI molecule. For example, the substituted polyethyleneimine compound may be formed by adding chlorinated tap water, by the addition of sodium hypochlorite, or by the addition of other halogenating agents. Halogenating agents include any compound capable of donating a halogen atom. Thus, halogenating agents include any compound that includes at least one electrophilic chlorine, bromine, fluorine, or iodine atom. Suitable examples of halogenating agents include, without limitation, bromine-containing compounds (such as N-bromosuccinimide and dibromohydantoin), chlorine-containing compounds (such as N-chlorosuccinimide, chlorite, sodium hypochlorite, chlorine dioxide, chloramine, dichlorohydantoin), iodine-containing compounds (such as N-iodosuccinimide), and fluorine-containing compounds. The reaction of substituted PEI with a halogenating agent may be carried out by bringing the halogenating agent to elevated temperature and then adding it to the substituted PEI (as shown in the Examples), or the halogenating agent may be provided at room temperature and added to the substituted PEI.

In this type of reaction, the percent substitution of the substituted polyethyleneimine compound when reacting with an acid may be calculated. In one aspect of the invention, the percent substitution of nitrogen atoms with alkyl or alkanoyl groups may be in the range from about 2% to about 15%. The percent substitution may depend upon the molecular weight of the specific PEI molecule utilized and whether the PEI molecule is linear or branched.

Electrophilic compounds include hydrocarbon-containing molecules having from about 2 to about 50 carbon atoms linearly arranged, or from about 5 to about 50 carbon atoms linearly arranged. In another aspect of the invention, electrophilic compounds include hydrocarbon-containing molecules having from about 10 to about 25 carbon atoms linearly arranged. Fatty acids are one class of suitable electrophilic compounds. Generally, a fatty acid consists of a straight chain of an even number of carbon atoms, with hydrogen atoms along the length of the chain and at one end of the chain and a carboxyl group (—COOH) at the other end. Suitable examples of electrophilic compounds include, without limitation, carboxylic acids, ketene dimers, formates, acetyl halides (such as acetyl chloride), esters, anhydrides, alkyl halides, epoxides, isocyanates, and the like, and mixtures thereof. In one aspect of the invention, the electrophilic compound is selected from the group consisting of stearic acid, isostearic acid, myristic acid, capric acid, lauric acid, palmitic acid, and mixtures thereof. In yet a further aspect of the invention, the electrophilic compound comprises an alkyl group, such as an alkyl halide. Preferably, the alkyl halide has ten or more carbon atoms, such as a $C_{10}$-$C_{30}$ alkyl halide.

In the general reaction scheme, the PEI molecule and the electrophilic compound are contacted at a temperature in the range from about 20° C. to about 180° C., or from about 40° C. to about 150° C., or from about 60° C. to about 150° C. The PEI molecule and electrophilic compounds are typically contacted for a period of time in the range from about 30 minutes to about 4 hours.

A method for preparing the odor control molecule of the present invention is comprised of the following steps:
  (a) providing a first polyethyleneimine compound comprising a plurality of amine groups; and
  (b) contacting the first polyethyleneimine compound with an electrophilic compound selected from the group consisting of carbonyl-containing compounds, alkyl halides, aryl halides, and epoxides in the presence of at least one additional halogen-containing composition, wherein the electrophilic compound reacts with an amine group of the first polyethyleneimine compound, and the at least one additional halogen-containing composition reacts with an amine group of the first polyethyleneimine compound to form the odor control molecule of the present invention.

A further method for preparing the odor control molecule of the present invention is comprised of the following steps:
  (a) providing a first polyethyleneimine compound comprising a plurality of amine groups;
  (b) contacting the first polyethyleneimine compound with at least one electrophilic compound selected from the group consisting of carbonyl-containing compounds, alkyl halides, aryl halides, and epoxides, wherein the electrophilic compound reacts with an amine group of the first polyethyleneimine compound to form a second polyethyleneimine compound; and (c) reacting the second polyethyleneimine compound with at least one halogen-containing composition, wherein the at least one halogen-containing composition reacts with an amine group of the first polyethyleneimine compound to form the odor control molecule of the present invention.

General structures of the polyethyleneimine composition containing N-halamine are shown below in Formula (A) and Formula (B):

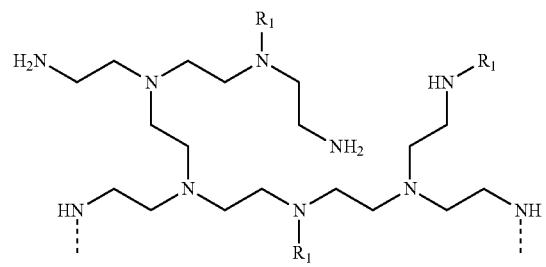

(A)

wherein each $R_1$ is independently selected from the group consisting of hydrogen, halogen, an alkyl group, an aryl group, an alkanoyl group, an alkenoyl group, and an aroyl group, and wherein at least one $R_1$ is halogen and at least one $R_1$ is selected from an aryl group, an alkanoyl group, an alkenoyl group, and an aroyl group; and

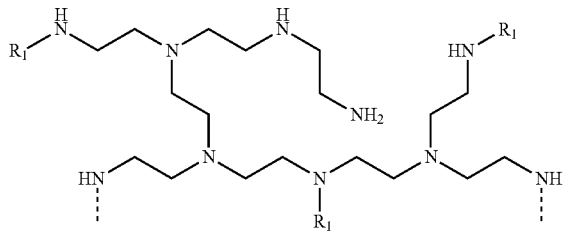

(B)

wherein each $R_1$ is independently selected from the group consisting of hydrogen, halogen, an alkyl group, an alkanoyl group, an alkenoyl group, and an aroyl group, and wherein at least one $R_1$ is halogen and at least one $R_1$ is selected from an aryl group, an alkanoyl group, an alkenoyl group, and an aroyl group.

The polyethyleneimine compound of Formula (A) and Formula (B) may further be characterized wherein at least one $R_1$ contains at least one polyalkyleneoxy chain, as further described below.

Additional general structures of the polyethyleneimine composition containing N-halamine are shown below in Formula (I) and Formula (II):

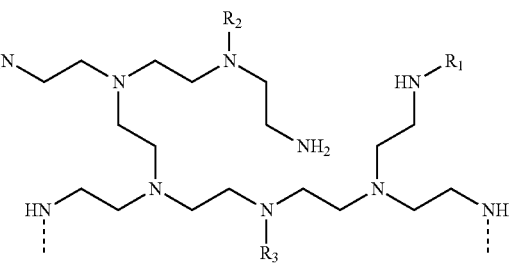

(I)

wherein $R_1$ and $R_2$ are independently selected from the group consisting of hydrogen, 02 to 050 alkyl, aryl, alkanoyl, alkenoyl, and aroyl; $R_3$ is halogen; and

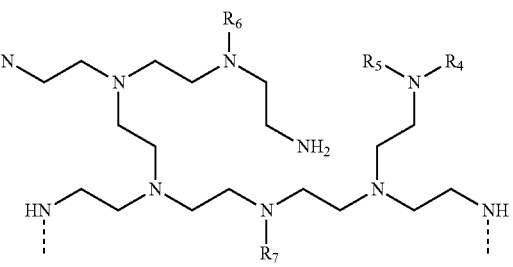

(II)

wherein each $R^4$, $R_5$, $R_6$ and $R_7$ is independently selected from the group consisting of hydrogen, halogen, aryl, alkanoyl, alkenoyl, and aroyl; wherein at least one of $R^4$, $R_5$, $R_6$ and $R_7$ is alkanoyl, alkenoyl, or aroyl; and wherein at least one of $R^4$, $R_5$, $R_6$ and $R_7$ is halogen.

The general structure of a chlorine-containing polyethyleneimine composition is shown below in Formula (III) and Formula (IV):

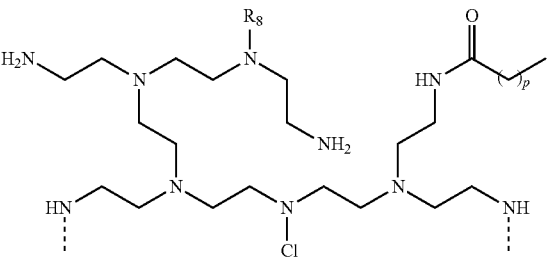

(III)

wherein $R_8$=hydrogen, alkyleneoxy, polyalkyleneoxy, alkyl, alkanoyl;

p=2 to 100 or p=5 to 50;

and

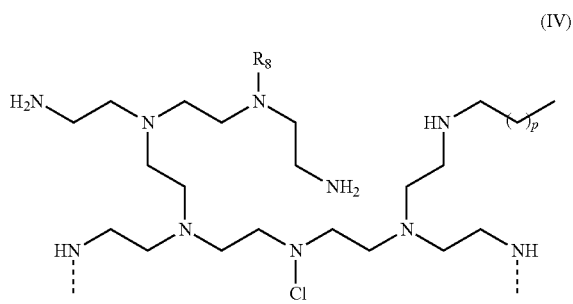

wherein $R_8$=hydrogen, alkyleneoxy, polyalkyleneoxy, alkyl, or alkanoyl;
p=2 to 100 or p=5 to 50.

In a further aspect of the invention, a chlorine-containing polyethyleneimine is shown below in Formula (V) and Formula (VI):

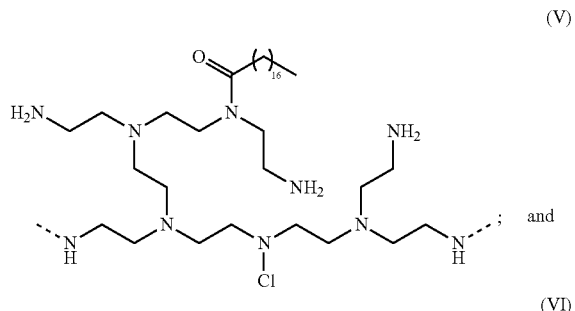

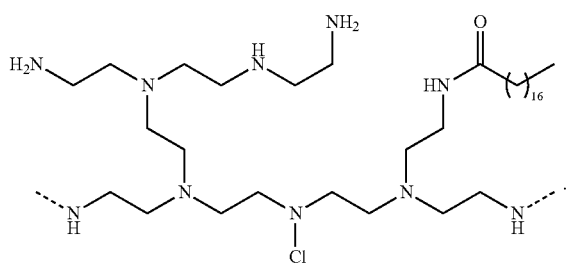

Synthesis of the substituted polyethyleneimine compound is carried out in the presence of at least one halogen-containing composition. As used herein, N-halamine is a compound containing one or more nitrogen-halogen covalent bonds that is normally formed by the halogenation of imide, amide, or amine groups. Halogen-containing compositions include compositions that contain at least one halogen atom. Halogen atoms include, for example, chlorine, bromine, fluorine, and iodine. Suitable halogen-containing compositions include, for example, tap water that contains halogen atoms (such as tap water that contains chlorine atoms), deionized water that contains an added halogenating species (such as deionized water that contains a chlorinating species), and mixtures thereof. For the sake of clarity, tap water is meant to describe any water that is readily obtainable from a faucet or other dispensing means and which is generally known to be treated with chlorine-containing compositions and therefore contains chlorine atoms. Thus, in one aspect of the present invention, the odor control molecule is formed by reacting polyethyleneimine with stearic acid in the presence of an aqueous chlorine-containing solution. The aqueous chlorine-containing solution may be selected from tap water (known to be treated with chlorine-containing compounds), deionized water having a halogenating species added thereto, or any other halogen-donating material capable of providing at least one halogen atom for bonding with at least one nitrogen atom, and mixtures thereof. Thus, the process for forming the odor control molecule includes chlorination or halogenation of the polyethyleneimine compound.

In one aspect of the invention, the molar ratio of polyethyleneimine molecules to electrophilic compounds is in the range from 1:1 to 1:500, or in the range from 1:1 to 1:250, or in the range from 1:1 to 1:100, or in the range from 1:1 to 1:50, or in the range from 1:1 to 1:25, or in the range from 1:1 to 1:10. In a further aspect of the invention, the molar ratio of polyethyleneimine molecules to electrophilic compounds is 1:3, 1:6 or 1:7.

It was discovered that, depending on the average molecular weight of the PEI raw material, the molar ratio of PEI to electrophilic compound could be tailored to provide improved odor control in treated textile substrates. For example, PEI having an average molecular weight of 25,000 is ideally reacted with an electrophilic compound in a ratio of 1:6 or 1:7. In another aspect of the invention, PEI having an average molecular weight of 10,000 is ideally reacted with an electrophilic compound in a ratio of 1:3. In yet a further aspect of the invention, PEI having an average molecular weight of 2000 is ideally reacted with an electrophilic compound in a ratio of 1:1. In all instances, there is at least one source of halogen atoms. It may be from tap water or from another source having halogen atoms contained therein (e.g. deionized water containing sodium hypochlorite).

At least one polyethyleneimine compound containing N-halamine as described herein may be added to a laundry care composition for use in controlling odor on textile substrates treated therewith. As a result, the invention also encompasses a textile substrate containing at least one polyethyleneimine compound containing N-halamine. The polyethyleneimine compound contains at least one N-halamine. The polyethyleneimine compound may contain two N-halamines, or even three N-halamines, or even four N-halamines. The invention further encompasses a process for controlling odor on a textile substrate that includes the steps of providing a textile substrate, applying and/or depositing at least one polyethyleneimine compound containing N-halamine as described herein to the textile substrate, and further agitating, rinsing, and/or drying the thus treated textile substrate.

Without being bound by theory, it is believed that one possible mechanism that may aid in the control of odor on textile substrates having the substituted polyethyleneimine compound deposited thereon includes the transfer of at least one proton from a volatile, foul-smelling, odor causing molecule. The transfer of the proton, in turn, neutralizes the odor causing molecule and prevents volatilization of the foul-smelling components from the treated surface. Odor causing molecules include, for example, acids, aldehydes, ketones, thiols, alcohols, aliphatic amines, aromatic amines, volatile aliphatic and aromatic compounds, and the like, and combinations thereof. Carboxylic acid represents one exemplary odor causing molecule from the acid group. Examples of such carboxylic acids include butyric acid, valeric acid, and isovaleric acid.

The substituted polyethyleneimine compound may be linear or branched. In another aspect of the invention, the substituted polyethyleneimine compound may be alkoxylated. Alkoxylation may be accomplished by first forming the substituted polyethyleneimine compound and then reacting this compound with at least one $C_1$-$C_8$ alkoxy or alkoxy derivative of polyol having repeating units. Alkoxylation is carried out by procedures well-known to those skilled in the art (see, for example, U.S. Pat. Nos. 4,137,243; 5,082,938; 5,135,972; 5,591,833; 6,593,483; 7,587,857; 9,056,963; and 9,068,081). Suitable $C_1$-$C_8$ alkoxy or alkoxy derivative of polyol having repeating units include alkylene oxides. Alkylene oxides may be selected from the group consisting of ethylene oxide, propylene oxide, butylene oxide, and mixtures thereof. Alkylene oxide groups may be in the form of polymeric chains known as polyalkyleneoxy chains. The term "polyalkyleneoxy," as used herein, generally refers to molecular structures containing the following repeating units: —$CH_2CH_2O$—, —$CH_2CH_2CH_2O$—, —$CH_2CH_2CH_2CH_2O$—, —$CH_2CH(CH_3)O$—, —$CH_2CH(CH_2CH_3)O$—$CH_2CH_2CH(CH_3)O$—, and any combinations thereof. Typical of such groups are the polymeric epoxides, such as the polyalkylene oxides and copolymers thereof. Typical polyalkylene oxides and copolymers of same include those made from alkylene oxide monomers containing from two to twenty carbon atoms, or more preferably, from two to six carbon atoms. Examples include: polyethylene oxides; polypropylene oxides; polybutylene oxides; oxetanes; tetrahydrafurans; copolymers of polyethylene oxides, polypropylene oxides and polybutylene oxides; and other copolymers including block copolymers, in which a majority of the polymeric substituent is polyethylene oxide, polypropylene oxide and/or polybutylene oxide. Further, such polyalkyleneoxy group may have an average molecular weight in the range of from about 132 to about 10,000, preferably from about 176 to about 5000.

Typically, the alkoxy molecules form caps for the ends of the chains comprising the odor control molecule. Thus, the resulting alkoxylated substituted polyethyleneimine compound may have an average degree of alkoxylation of from 0.5 to 50, or from 1 to 50, or from 1 to 30, or from 1 to 20, or from 1 to 10, or from 2 to 50, or from 2 to 30, or from 2 to 20, or from 2 to 10, or from 3 to 50 or from 3 to 30, or from 3 to 20, or from 3 to 10, or from 4 to 50, or from 4 to 30, or from 4 to 20, or from 4 to 10.

While the invention described herein has been directed mainly to polyethyleneimine compositions, it is not limited to only those compositions. The electrophilic compounds, halogen-containing materials, and polyalkyleneoxy materials described herein may also be reacted with other polyalkyleneimine compounds. Thus, the odor control molecule of the present invention may be a polyalkyleneimine compound containing N-halamine. Polyalkyleneimine compounds include polyalkyleneoxy substituted materials wherein propyleneoxy units, butyleneoxy units, and mixtures thereof are attached to the backbone nitrogen atoms prior to subsequent attachment of polyethyleneoxy units. Further description of these compounds may be found in U.S. Pat. No. 6,127,331 to Cleary et al., which is entirely incorporated by reference herein.

Thus, in one aspect of the invention, the odor control molecule is a polyethyleneimine molecule containing at least one N—X moiety and at least one alkanoyl, alkenoyl, aroyl, aryl, or alkyl group, wherein X is a halogen atom (such as Cl, Br, I, or F). In another aspect of the invention, the odor control molecule is a polyethyleneimine molecule containing at least one N—X moiety, wherein X is a halogen atom (such as Cl, Br, I, or F), and at least one alkanoyl group and at least one alkyl group. In a further aspect of the invention, the odor control molecule is a polyethyleneimine molecule containing at least one N—X moiety, wherein X is a halogen atom (such as Cl, Br, I, or F), at least one alkanoyl group, and at least one polyalkyleneoxy chain. In yet another aspect of the invention, the odor control molecule is a polyethyleneimine molecule containing at least one N—X moiety, wherein X is a halogen atom (such as Cl, Br, I, or F), at least one alkyl group, and at least one polyalkyleneoxy chain. In yet a further aspect of the invention, the odor control molecule is a polyethyleneimine molecule containing at least one N—X moiety, wherein X is a halogen atom (such as Cl, Br, I, or F), and at least one polyalkyleneoxy chain. In another aspect of the invention, the odor control molecule is a polyethyleneimine molecule containing at least one N—X moiety, wherein X is a halogen atom (such as Cl, Br, I, or F), at least one alkanoyl group, at least one alkyl group, and at least one polyalkyleneoxy chain.

It has further been discovered that the odor control molecule of the present invention also possesses the ability to improve wicking on materials treated therewith. As is known in the textile arts, the term "wicking" is generally intended to refer to dispersing or spreading of moisture or liquid through a given area, vertically and/or horizontally. Improvement in wicking has been observed on textile substrates treated with the odor control molecule of the present invention. One suitable test for evaluating wicking is known as the "Drop Wick Test."

It was observed that the odor molecule when added in the wash helped the wicking ability for multiple washes for polyester and other blends. The branched amine portion present in the odor molecule helps in the wicking ability. The odor molecule can also be encapsulated with polymers to be released slowly in the wash.

In one aspect of the present invention, odor control molecules containing branched, chains exhibited better wicking performance. Without being bound by theory, it is believed that odor control molecules containing branched chains exhibit better wicking performance. The improvement in wicking provided by the odor control molecule is rejuvenated each time a textile substrate is exposed to the molecule during the laundering process.

It is also contemplated to be within the scope of the present invention that the odor control molecule may be encapsulated. Encapsulation of the odor control molecule may provide a delivery system for delivering the odor control molecule to a substrate treated therewith. Encapsulation may be achieved by blending the odor control molecule with an encapsulation material to form a mixture. Encapsulation materials include, for example, polymeric materials. The polymeric material used for encapsulation may be a water-soluble polymer of neutral charge. Exemplary water-soluble polymers may be selected from the group consisting of polyethylene glycol, polyvinyl glycol, polyvinylpyrrolidone, block copolymers of ethylene oxide and propylene oxide, and combinations thereof.

Textile substrates treated with the odor control molecule of the present invention may be comprised of synthetic fibers, natural fibers, or combinations of synthetic and natural fibers. Synthetic fibers include, for example, polyester, acrylic, polyamide, polyolefin, polyaramid, polyurethane, regenerated cellulose (i.e., rayon), and blends thereof. The term "polyamide" is intended to describe any long-chain polymer having recurring amide groups (—NH—CO—) as an integral part of the polymer chain. Examples of polyamides include nylon 6; nylon 6, 6; nylon 1, 1; and nylon 6, 10. The term "polyester" is intended to describe any long-chain polymer having recurring ester groups (—C (O)—O—). Examples of polyesters include aromatic polyesters, such as polyethylene terephthalate (PET), polybutylene terephthalate (PBT), polytrimethylene terephthalate (PTT), and polytriphenylene terephthalate, and aliphatic polyesters, such as polylactic acid (PLA). "Polyolefin" includes, for example, polypropylene, polyethylene, and combinations thereof. "Polyaramid" includes, for example, poly-p-phenyleneteraphthalamid (i.e., Kevlar®), poly-m-phenyleneteraphthalamid (i.e., Nomex®), and combinations thereof. Natural fibers include, for example, wool, cotton, flax, and blends thereof.

The textile substrate may be formed from fibers or yarns of any size, including microdenier fibers and yarns (fibers or yarns having less than one denier per filament). The fibers or yarns may have deniers that range from less than about 1 denier per filament to about 2000 denier per filament or more preferably, from less than about 1 denier per filament to about 500 denier per filament, or even more preferably, from less than about 1 denier per filament to about 300 denier per filament.

Furthermore, the textile substrate may be partially or wholly comprised of multi-component or bi-component fibers or yarns, which may be splittable, or which have been partially or fully split, along their length by chemical or mechanical action. The textile substrate may be comprised of fibers such as staple fiber, filament fiber, spun fiber, or combinations thereof.

The textile substrate may be of any variety, including but not limited to, woven fabric, knitted fabric, nonwoven fabric, or combinations thereof. The textile substrate may optionally be colored by a variety of dyeing techniques, such as high temperature jet dyeing with disperse dyes, vat dyeing, thermosol dyeing, pad dyeing, transfer printing, screen printing, or any other technique that is common in the art for comparable textile products. The yarns or fibers comprising the textile substrate may optionally be dyed by suitable methods prior to fabric formation, such as, for instance, by package dyeing or solution dyeing.

Textile substrates include, for example, articles of apparel, such as outerwear (e.g., rainwear), workwear (e.g., uniforms), fashion apparel (e.g., shirts, pants, and other garments); drapery; napery (e.g., table linens and napkins); residential upholstery; commercial upholstery; automotive upholstery; wall coverings; floorcovering articles (e.g., carpets, rugs and mats); human bedding (e.g., mattresses, mattress covers, and the like); pet bedding; outdoor fabric (e.g., outdoor furniture, awnings, boat covers, and grill covers); medical dressings (e.g., fabrics for use in wound care); and any other article capable of possessing malodor and wherein it is desirable to control said malodor.

The odor control molecule of the present invention may be combined with other odor control agents useful for providing chemical treatments to textile substrates. Other odor control agents include antimicrobial agents, antibacterial agents, perfumes, activated carbon, carbon black, activated charcoal, graphene, metal organic frameworks, zeolites, antioxidants, and the like, and combinations thereof. Non-limiting examples of antimicrobial agents include chitosan, cyclodextrin, and mixtures thereof. Thus, in one aspect of the invention, a polyethyleneimine compound containing N-halamine is combined with chitosan for use in controlling odor. In another aspect of the invention, a polyethyleneimine compound containing N-halamine is combined with cyclodextrin for use in controlling odor. In yet a further aspect of the invention, a polyethyleneimine compound containing N-halamine is combined with activated carbon for use in controlling odor. In a further aspect of the invention, a polyethyleneimine compound containing N-halamine is combined with perfume for use in controlling odor.

The substituted polyethyleneimine compound of the present invention may be incorporated into a laundry care composition including but not limited to laundry detergents and fabric treatment compositions. As used herein, the term "laundry care composition" includes, unless otherwise indicated, granular, powder, liquid, gel, paste, unit dose bar form and/or flake type washing agents and/or fabric treatment compositions. As used herein, the term "fabric treatment composition" includes, unless otherwise indicated, fabric softening compositions, fabric enhancing compositions, fabric freshening compositions, and combinations thereof. Such compositions may be, but need not be, rinse added compositions. The odor control molecule incorporated into the laundry care composition may be comprised of the halogen-containing PEI-acid complex, the alkoxylated halogen-containing PEI-complex, or mixtures thereof.

Laundry care compositions of the present invention comprise one or more of said odor control molecules (i.e., the substituted PEI molecules as described herein) and a laundry care ingredient. The odor control molecule may be added to substrates using a variety of application techniques. For application to textile substrates, the odor control molecule is preferably included as an additive in laundry detergent. Thus, application to the textile substrate actually occurs when a consumer adds laundry detergent to a washing machine. Similarly, rinse added fabric softening ("RAFS") compositions are typically added in the rinse cycle, which is after the detergent solution has been used and replaced with the rinsing solution in typical laundering processes.

The laundry care compositions including laundry detergents may be in solid or liquid form, including a gel form. The laundry care compositions including laundry detergents may also be in a unit dose pouch. The laundry detergent composition comprises a surfactant in an amount sufficient to provide desired cleaning properties.

The odor control molecule may be present in the laundry care composition (such as the laundry detergent composition) in an amount from about 0.0001% to about 10% by weight of the composition, more preferably from about 0.0001% to about 5% by weight of the composition, and even more preferably from about 0.0001% to about 1% by weight of the composition.

The laundry detergent composition comprises a surfactant in an amount sufficient to provide desired cleaning properties. In one embodiment, the laundry detergent composition comprises, by weight, from about 5% to about 90% of the surfactant, and more specifically from about 5% to about 70% of the surfactant, and even more specifically from about 5% to about 40%. The surfactant may comprise anionic, nonionic, cationic, zwitterionic and/or amphoteric surfactants. In a more specific embodiment, the detergent composition comprises anionic surfactant, nonionic surfactant, or mixtures thereof.

Suitable anionic surfactants useful herein can comprise any of the conventional anionic surfactant types typically used in liquid detergent products. These include the alkyl benzene sulfonic acids and their salts as well as alkoxylated or non-alkoxylated alkyl sulfate materials.

Exemplary anionic surfactants are the alkali metal salts of $C_{10-16}$ alkyl benzene sulfonic acids, preferably $C_{11-14}$ alkyl benzene sulfonic acids. Preferably the alkyl group is linear and such linear alkyl benzene sulfonates are known as "LAS". Alkyl benzene sulfonates, and particularly LAS, are well known in the art. Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$, e.g., $C_{12}$, LAS is a specific example of such surfactants.

Another exemplary type of anionic surfactant comprises ethoxylated alkyl sulfate surfactants. Such materials, also known as alkyl ether sulfates or alkyl polyethoxylate sulfates, are those which correspond to the formula: R'—O—$(C_2H_4O)_n$—$SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6 or even from about 1 to 3 or from about 1 to 1.5 and M is sodium.

The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the compositions of this invention and used as or in any anionic surfactant component which may be present. Specific examples of non-alkoxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $ROSO_3$-$M^+$ wherein R is typically a linear $C_8$-$C_{20}$ hydrocarbyl group, which may be straight chain or branched chain, and M is a water-solubilizing cation. In specific embodiments, R is a $C_{10}$-$C_{15}$ alkyl, and M is alkali metal, more specifically R is $C_{12}$-$C_{14}$ and M is sodium.

Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{11}$ secondary (2,3) alkyl sulfates; d) $C_{10}$-$C_{18}$ alkyl alkoxy sulfates ($AE_xS$) wherein preferably x is from 1-30; e) $C_{10}$-$C_{18}$ alkyl alkoxy carboxylates preferably comprising 1-5 ethoxy units; f) mid-chain branched alkyl sulfates as discussed in U.S. Pat. No. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

Suitable nonionic surfactants useful herein can comprise any of the conventional nonionic surfactant types typically used in liquid detergent products. These include alkoxylated fatty alcohols and amine oxide surfactants. Preferred for use in the liquid detergent products herein are those nonionic surfactants which are normally liquid.

Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_8$-$C_{16}$ alkyl group, m is from 2 to 4, and n ranges from about 2 to 12. Preferably $R^1$ is an alkyl group, which may be primary or secondary, that comprises from about 9 to 15 carbon atoms, more preferably from about 10 to 14 carbon atoms. In one embodiment, the alkoxylated fatty alcohols will also be ethoxylated materials that contain from about 2 to 12 ethylene oxide moieties per molecule, more preferably from about 3 to 10 or even from about 7 to 9 ethylene oxide moieties per molecule.

The alkoxylated fatty alcohol materials useful in the liquid detergent compositions herein will frequently have a hydrophilic-lipophilic balance (HLB) which ranges from about 3 to 17. More preferably, the HLB of this material will range from about 6 to 15, most preferably from about 8 to 15. Alkoxylated fatty alcohol nonionic surfactants have been marketed under the tradenames Neodol and Dobanol by the Shell Chemical Company.

Another suitable type of nonionic surfactant useful herein comprises the amine oxide surfactants. Amine oxides are materials which are often referred to in the art as "semi-polar" nonionics. Amine oxides have the formula: $R(EO)_x(PO)_y(BO)_zN(O)(CH_2R')_2 \cdot qH_2O$. In this formula, R is a relatively long-chain hydrocarbyl moiety which can be saturated or unsaturated, linear or branched, and can contain from 8 to 20, preferably from 10 to 16 carbon atoms, and is more preferably $C_{12}$-$C_{16}$ primary alkyl. R' is a short-chain moiety, preferably selected from hydrogen, methyl and —$CH_2OH$. When x+y+z is different from 0, EO is ethyleneoxy, PO is propyleneoxy and BO is butyleneoxy. Amine oxide surfactants are illustrated by $C_{12-14}$ alkyldimethyl amine oxide.

Non-limiting examples of nonionic surfactants include: a) $C_{12}$-$C_{18}$ alkyl ethoxylates, such as, NEODOL® nonionic surfactants from Shell; b) $C_6$-$C_{12}$ alkyl phenol alkoxylates wherein the alkoxylate units are a mixture of ethyleneoxy and propyleneoxy units; c) $C_{12}$-$C_{18}$ alcohol and $C_6$-$C_{12}$ alkyl phenol condensates with ethylene oxide/propylene oxide block polymers such as Pluronic® from BASF; d) $C_{14}$-$C_{22}$ mid-chain branched alcohols, BA, as discussed in U.S. Pat. No. 6,150,322; e) $C_{14}$-$C_{22}$ mid-chain branched alkyl alkoxylates, $BAE_x$, wherein x if from 1-30, as discussed in U.S. Pat. Nos. 6,153,577, 6,020,303 and 6,093,856; f) Alkylpolysaccharides as discussed in U.S. Pat. No. 4,565,647 to Llenado, issued Jan. 26, 1986; specifically alkylpolyglycosides as discussed in U.S. Pat. Nos. 4,483,780 and 4,483,779; g) Polyhydroxy fatty acid amides as discussed in U.S. Pat. No. 5,332,528, WO 92/06162, WO 93/19146, WO 93/19038, and WO 94/09099; and h) ether capped poly(oxyalkylated) alcohol surfactants as discussed in U.S. Pat. No. 6,482,994 and WO 01/42408.

In the laundry detergent compositions herein, the detersive surfactant component may comprise combinations of anionic and nonionic surfactant materials. When this is the case, the weight ratio of anionic to nonionic will typically range from 10:90 to 90:10, more typically from 30:70 to 70:30.

Cationic surfactants are well known in the art and non-limiting examples of these include quaternary ammonium surfactants, which can have up to 26 carbon atoms. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002, WO 98/35003, WO 98/35004, WO 98/35005, and WO 98/35006; d) cationic ester surfactants as discussed in U.S. Pat. Nos. 4,228,042, 4,239,660 4,260,529 and U.S. Pat. No. 6,022,844; and e) amino surfactants as discussed in U.S. Pat. No. 6,221,825 and WO 00/47708, specifically amido propyldimethyl amine (APA).

Non-limiting examples of zwitterionic surfactants include derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants; betaine, including alkyl dimethyl betaine and cocodimethyl amidopropyl betaine, $C_8$ to $C_{18}$ (preferably $C_{12}$ to $C_{18}$) amine oxides and sulfo and hydroxy betaines, such as N-alkyl-N,N-dimethylamino-1-propane sulfonate where the alkyl group can be $C_8$ to $C_{18}$, preferably $C_{10}$ to $C_{14}$.

Non-limiting examples of ampholytic surfactants include aliphatic derivatives of secondary or tertiary amines, or aliphatic derivatives of heterocyclic secondary and tertiary amines in which the aliphatic radical can be straight- or branched-chain. One of the aliphatic substituents comprises at least about 8 carbon atoms, typically from about 8 to about 18 carbon atoms, and at least one comprises an anionic water-solubilizing group, e.g. carboxy, sulfonate, sulfate. See U.S. Pat. No. 3,929,678 to Laughlin et al., issued Dec. 30, 1975 at column 19, lines 18-35, for examples of ampholytic surfactants.

As noted, the compositions may be in the form of a solid, either in tablet or particulate form, including, but not limited to particles, flakes, or the like, or the compositions may be in the form of a liquid. The liquid detergent compositions comprise an aqueous, non-surface active liquid carrier. Generally, the amount of the aqueous, non-surface active liquid carrier employed in the compositions herein will be effective to solubilize, suspend or disperse the composition components. For example, the compositions may comprise, by weight, from about 5% to about 90%, more specifically from about 10% to about 70%, and even more specifically from about 20% to about 70% of the aqueous, non-surface active liquid carrier.

The most cost-effective type of aqueous, non-surface active liquid carrier is, of course, water itself. Accordingly, the aqueous, non-surface active liquid carrier component will generally be mostly, if not completely, comprised of water. However, other types of water-miscible liquids, such as alkanols, diols, other polyols, ethers, amines, and the like, and mixtures thereof, may also be added to liquid detergent compositions as co-solvents or stabilizers in addition to or in place of water. Accordingly, the aqueous non-surface active liquid carrier component of the liquid detergent composition will generally be present in concentrations ranging from about 5% to about 90% by weight of the composition, more preferably from about 20% to about 70% by weight of the composition.

Detergent compositions may also contain bleaching agents. Suitable bleaching agents include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A suitable percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

Compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

(a) Bleach Activators—

Preferably, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide, source leads to the in situ production of the peracid corresponding to the bleach activator. Various non-limiting examples of activators are disclosed in U.S. Pat. Nos. 5,576,282; 4,915,854 and 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzene-sulphonate (NOBS), phenyl benzoate (PhBz), decanoyloxybenzenesulphonate ($C_{10}$—OBS), benzoylvalerolactam (BZVL), octanoyloxybenzenesulphonate ($C_8$—OBS), perhydrolyzable esters and mixtures thereof, most preferably benzoylcaprolactam and benzoytvalerolactam. Particularly preferred bleach activators in the pH range from about 8 to about 11 are those selected having an OBS or VL leaving group.

Preferred hydrophobic bleach activators include, but are not limited to, nonanoyloxybenzenesulphonate (NOBS); 4-[N-(nonanoyl) amino hexanoyloxy]-benzene sulfonate sodium salt (NACA-OBS), an example of which is described in U.S. Pat. No. 5,523,434; dodecanoyloxybenzenesulphonate (LOBS or $C_{12}$—OBS); 10-undecenoyloxybenzenesulfonate (UDOBS or $C_{11}$—OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., and copending patent application Ser. No. 08/064,564, all of which are incorporated herein by reference.

The mole ratio of peroxygen source (as AvO) to bleach activator in the present invention generally ranges from at least 1:1, preferably from about 20:1, more preferably from about 10:1 to about 1:1, preferably to about 3:1.

Quaternary substituted bleach activators may also be included. The present laundry compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Highly preferred bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl) oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)═N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, are very useful herein, especially the acyl caprolactams (see for example WO 94-28102 A) and acyl valerolactams (see U.S. Pat. No. 5,503,639 to Willey et al. incorporated herein by reference).

(b) Organic Peroxides, Especially Diacyl Peroxides—

These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

(c) Metal-Containing Bleach Catalysts—

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

Manganese Metal Complexes—

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn^{IV}_2(u-O)_3(1,4,7$-trimethyl-1,4,7-triazacyclononane$)_2$-$(PF_6)_2$, $Mn^{III}_2(u-O)_1(u$-OAc$)_2(1,4,7$-trimethyl-1,4,7-triazacyclononane$)_2(ClO_4)_2$, $Mn^{IV}_4(u-O)_6(1,4,7$-triazacyclononane$)_4(ClO_4)_4$, $Mn^{III}Mn^{IV}_4(u-O)_1(u$-OAc$)_2$-$(1,4,7$-trimethyl-1,4,7-triazacyclononane$)_2(ClO_4)_3$, $Mn^{IV}(1,4,7$-trimethyl-1,4,7-triazacyclononane$)$-$(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt Metal Complexes—

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorg. Bioinorg. Mech.*, (1983), 2, pages 1-94. The most preferred cobalt catalyst useful herein are cobalt pentaamine acetate salts having the formula [Co(NH$_3$)$_5$OAc] Ty, wherein "OAc" represents an acetate moiety and "Ty" is an anion, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF$_4$)$_2$; and [Co(NH$_3$)$_5$OAc](NO$_3$)$_2$(herein "PAC").

These cobalt catalysts are readily prepared by known procedures, such as taught for example in U.S. Pat. Nos. 6,302,921; 6,287,580; 6,140,294; 5,597,936; 5,595,967; and 5,703,030; in the Tobe article and the references cited therein; and in U.S. Pat. No. 4,810,410; *J. Chem. Ed.* (1989), 6 (12), 1043-45; The Synthesis and Characterization of Inorganic Compounds, W. L. Jolly (Prentice-Hall; 1970), pp. 461-3; *Inorg. Chem.*, 18, 1497-1502 (1979); *Inorg. Chem.*, 21, 2881-2885 (1982); *Inorg. Chem.*, 18, 2023-2025 (1979); *Inorg. Synthesis*, 173-176 (1960); and *Journal of Physical Chemistry*, 6, 22-25 (1952).

Transition Metal Complexes of Macropolycyclic Rigid Ligands—

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or laundry uses, and are non-limitingly illustrated by any of the following:

Dichloro-5,12-dimethyl-1,5,8,12-tetraazabicyclo[6.6.2] hexadecane Manganese(II)

Dichloro-5,12-diethyl-1,5,8,12-tetraazabicyclo[6.6.2]hexadecane Manganese(II)

Diaquo-5,12-dimethyl-1,5,8,12-tetraazabicyclo[6.6.2]hexadecaneManganese(II) Hexafluorophosphate Diaquo-5,12-diethyl-1,5,8,12-tetraazabicyclo[6.6.2]hexadecaneManganese(II) Hexafluorophosphate Aquo-hydroxy-5,12-dimethyl-1,5,8,12-tetraazabicyclo [6.6.2]hexadecane Manganese(III) Hexafluorophosphate Diaquo-5,12-dimethyl-1,5,8,12-tetraazabicyclo[6.6.2]hexadecaneManganese(II) Tetrafluoroborate Dichloro-5,12-dimethyl-1,5,8,12 tetraazabicyclo[6.6.2] hexadecane Manganese(III) Hexafluorophosphate Dichloro-5,12-diethyl-1,5,8,12-tetraazabicyclo[6.6.2]hexadecaneManganese(III) Hexafluorophosphate Dichloro-5,12-di-n-butyl-1,5,8,12-tetraaza bicyclo[6.6.2] hexadecane Manganese(II)

Dichloro-5,12-dibenzyl-1,5,8,12-tetraazabicyclo[6.6.2] hexadecaneManganese(II)

Dichloro-5-n-butyl-12-methyl-1,5,8,12-tetraaza-bicyclo [6.6.2]hexadecane Manganese(II)

Dichloro-5-n-octyl-12-methyl-1,5,8,12-tetraaza-bicyclo [6.6.2]hexadecane Manganese(II)

Dichloro-5-n-butyl-12-methyl-1,5,8,12-tetraaza-bicyclo [6.6.2]hexadecane Manganese(II).

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

(d) Bleach Boosting Compounds—

The compositions herein may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

[A]

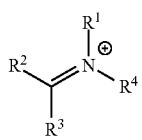

where $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source employed in the present invention may comprise any of these well known sources, including peroxygen compounds as well as compounds, which under consumer use conditions, provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. The bleach boosting compounds, when present, are preferably employed in conjunction with a peroxygen source in the bleaching systems of the present invention.

(e) Preformed Peracids—

Also suitable as bleaching agents are preformed peracids. The preformed peracid compound as used herein is any convenient compound which is stable and which under consumer use conditions provides an effective amount of peracid or peracid anion. The preformed peracid compound may be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

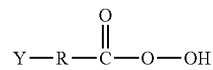

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

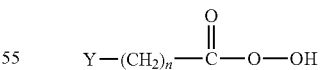

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

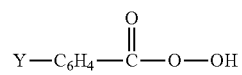

wherein Y can be, for example, hydrogen, alkyl, alkyihalogen, halogen, C(O)OH or C(O)OOH.

Typical monoperoxy acids useful herein include alkyl and aryl peroxyacids such as:

(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);

(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);

(iii) amidoperoxyacids, e.g. mononopylamide of either peroxysuccinic acid (NAPSA) or of peroxyadipic acid (NAPAA).

Typical diperoxyacids useful herein include alkyl diperoxyacids and aryldiperoxyacids, such as:

(i) 1,1 2-diperoxydodecanedioic acid;
(ii) 1,9-diperoxyazelaic acid;
(iii) diperoxybrassylic acid; diperoxysebacic acid and diperoxyisophthalic acid;
(iv) 2-decyldiperoxybutane-1,4-dioic acid;
(v) 4,4'-sulfonylbisperoxybenzoic acid.

Such bleaching agents are disclosed in U.S. Pat. No. 4,483,781 to Hartman and U.S. Pat. No. 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, Del. can also be employed as a suitable source of peroxymonosulfuric acid. PAP is disclosed in, for example, U.S. Pat. Nos. 5,487,818; 5,310,934; 5,246,620; 5,279,757 and 5,132,431.

(f) Photobleaches—

Suitable photobleaches for use in the treating compositions of the present invention include, but are not limited to, the photobleaches described in U.S. Pat. Nos. 4,217,105 and 5,916,481.

(g) Enzyme Bleaching—

Enzymatic systems may be used as bleaching agents. The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

The present invention compositions and methods may utilize alternative bleach systems such as ozone, chlorine dioxide and the like. Bleaching with ozone may be accomplished by introducing ozone-containing gas having ozone content from about 20 to about 300 g/m$^3$ into the solution that is to contact the fabrics. The gas:liquid ratio in the solution should be maintained from about 1 2.5 to about 1:6. U.S. Pat. No. 5,346,588 describes a process for the utilization of ozone as an alternative to conventional bleach systems and is herein incorporated by reference.

The detergent compositions of the present invention may also include any number of additional optional ingredients. These include conventional laundry detergent composition components such as non-tinting dyes, detersive builders, enzymes, enzyme stabilizers (such as propylene glycol, boric acid and/or borax), suds suppressors, soil suspending agents, soil release agents, other fabric care benefit agents, pH adjusting agents, chelating agents, smectite clays, solvents, hydrotropes and phase stabilizers, structuring agents, dye transfer inhibiting agents, opacifying agents, optical brighteners, perfumes and coloring agents. The various optional detergent composition ingredients, if present in the compositions herein, should be utilized at concentrations conventionally employed to bring about their desired contribution to the composition or the laundering operation. Frequently, the total amount of such optional detergent composition ingredients can range from about 0.01% to about 50%, more preferably from about 0.1% to about 30%, by weight of the composition.

The liquid detergent compositions are in the form of an aqueous solution or uniform dispersion or suspension of surfactant, odor control molecule, and certain optional other ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable and will typically have a viscosity which ranges from about 100 to 600 cps, more preferably from about 150 to 400 cps. For purposes of this invention, viscosity is measured with a Brookfield LVDV-II+ viscometer apparatus using a #21 spindle.

The liquid detergent compositions herein can be prepared by combining the components thereof in any convenient order and by mixing, e.g., agitating, the resulting component combination to form a phase stable liquid detergent composition. In a preferred process for preparing such compositions, a liquid matrix is formed containing at least a major proportion, and preferably substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In an alternate embodiment for forming the liquid detergent compositions, the odor control molecule is first combined with one or more liquid components to form an odor control molecule premix, and this odor control molecule premix is added to a composition formulation containing a substantial portion, for example more than 50% by weight, more specifically, more than 70% by weight, and yet more specifically, more than 90% by weight, of the balance of components of the laundry detergent composition. For example, in the methodology described above, both the odor control molecule premix and the enzyme component are added at a final stage of component additions. In a further embodiment, the odor control molecule is encapsulated prior to addition to the detergent composition, the encapsulated odor control molecule is suspended in a structured liquid, and the suspension is added to a composition formulation containing a substantial portion of the balance of components of the laundry detergent composition.

As noted previously, the detergent compositions may be in a solid form. Suitable solid forms include tablets and particulate forms, for example, granular particles or flakes. Various techniques for forming detergent compositions in such solid forms are well known in the art and may be used herein. In one embodiment, for example when the composition is in the form of a granular particle, the odor control molecule is provided in particulate form, optionally including additional but not all components of the laundry detergent composition. The odor control molecule particulate is combined with one or more additional particulates containing a balance of components of the laundry detergent composition. Further, the odor control molecule, optionally including additional but not all components of the laundry detergent composition, may be provided in an encapsulated form, and the odor control molecule encapsulate is combined with particulates containing a substantial balance of components of the laundry detergent composition.

The compositions of this invention, prepared as hereinbefore described, can be used to form aqueous washing solutions for use in the laundering of textile substrates such as fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the liquid detergent compositions herein added to water to form aqueous laundering solutions can comprise amounts sufficient to form from about 500 to 7,000 ppm of composition in aqueous washing solution. More preferably, from about 1,000 to 3,000 ppm of the detergent compositions herein will be provided in aqueous washing solution.

Fabric Treatment Compositions/Rinse Added Fabric Softening Compositions

In another specific embodiment, the odor control molecules of the present invention may be included in a fabric treatment composition. The fabric treatment composition may be comprised of at least one odor control molecule and a rinse added fabric softening composition ("RAFS;" also known as rinse added fabric conditioning compositions). Examples of typical rinse added softening compositions can be found in U.S. Provisional Patent Application Ser. No. 60/687,582 filed on Oct. 8, 2004. The rinse added fabric softening compositions of the present invention may comprise (a) fabric softening active ("FSA") and (b) an odor control molecule. The rinse added fabric softening composition may comprise from about 1% to about 90% by weight of the FSA, more preferably from about 5% to about 50% by weight of the FSA. The odor control molecule may be present in the rinse added fabric softening composition in an amount from about 0.5 ppb to about 50 ppm, more preferably from about 0.5 ppm to about 30 ppm.

In one embodiment of the invention, the fabric softening active is a quaternary ammonium compound suitable for softening fabric in a rinse step. In one embodiment, the FSA is formed from a reaction product of a fatty acid and an aminoalcohol obtaining mixtures of mono-, di-, and, in one embodiment, triester compounds. In another embodiment, the FSA comprises one or more softener quaternary ammonium compounds such, but not limited to, as a monoalkyquaternary ammonium compound, a diamido quaternary compound and a diester quaternary ammonium compound, or a combination thereof.

In one aspect of the invention, the FSA comprises a diester quaternary ammonium (hereinafter "DQA") compound composition. In certain embodiments of the present invention, the DQA compounds compositions also encompasses a description of diamido FSAs and FSAs with mixed amido and ester linkages as well as the aforementioned diester linkages, all herein referred to as DQA.

A first type of DQA ("DQA (1)") suitable as a FSA includes a compound comprising the formula:

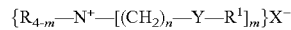

wherein each R substituent is either hydrogen, a short chain $C_1$-$C_6$, preferably $C_1$-$C_3$ alkyl or hydroxyalkyl group, e.g., methyl (most preferred), ethyl, propyl, hydroxyethyl, and the like, poly ($C_{2-3}$ alkoxy), preferably polyethoxy, group, benzyl, or mixtures thereof; each m is 2 or 3; each n is from 1 to about 4, preferably 2; each Y is —O—(O)C—, —C(O)—O—, —NR—C(O)—, or —C(O)—NR— and it is acceptable for each Y to be the same or different; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate. Preferred DQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids, e.g., tallow, hardened tallow, oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, palm oil, etc.

Non-limiting examples of suitable fatty acids are listed in U.S. Pat. No. 5,759,990 at column 4, lines 45-66. In one embodiment, the FSA comprises other actives in addition to DQA (1) or DQA. In yet another embodiment, the FSA comprises only DQA (1) or DQA and is free or essentially free of any other quaternary ammonium compounds or other actives. In yet another embodiment, the FSA comprises the precursor amine that is used to produce the DQA.

In another aspect of the invention, the FSA comprises a compound, identified as DTTMAC comprising the formula:

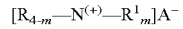

wherein each m is 2 or 3, each $R^1$ is a $C_6$-$C_{22}$, preferably $C_{14}$-$C_{20}$, but no more than one being less than about $C_{12}$ and then the other is at least about 16, hydrocarbyl, or substituted hydrocarbyl substituent, preferably $C_{10}$-$C_{20}$ alkyl or alkenyl (unsaturated alkyl, including polyunsaturated alkyl, also referred to sometimes as "alkylene"), most preferably $C_{12}$-$C_{18}$ alkyl or alkenyl, and branch or unbranched. In one embodiment, the Iodine Value (IV) of the FSA is from about 1 to 70; each R is H or a short chain $C_1$-$C_6$, preferably $C_1$-$C_3$ alkyl or hydroxyalkyl group, e.g., methyl (most preferred), ethyl, propyl, hydroxyethyl, and the like, benzyl, or $(R^2O)_{2-4}H$ where each $R^2$ is a $C_{1-6}$ alkylene group; and $A^-$ is a softener compatible anion, preferably, chloride, bromide, methylsulfate, ethylsulfate, sulfate, phosphate, or nitrate; more preferably chloride or methyl sulfate.

Examples of these FSAs include dialkydimethylammonium salts and dialkylenedimethylammonium salts such as ditallowdimethylammonium and ditallowdimethylammonium methylsulfate. Examples of commercially available dialkylenedimethylammonium salts usable in the present invention are di-hydrogenated tallow dimethyl ammonium chloride and ditallowdimethyl ammonium chloride available from Degussa under the trade names Adogen® 442 and Adogen® 470 respectively. In one embodiment, the FSA comprises other actives in addition to DTTMAC. In yet another embodiment, the FSA comprises only compounds of the DTTMAC and is free or essentially free of any other quaternary ammonium compounds or other actives.

In one embodiment, the FSA comprises an FSA described in U.S. Pat. Pub. No. 2004/0204337 A1, published Oct. 14, 2004 to Corona et al., from paragraphs 30-79. In another embodiment, the FSA is one described in U.S. Pat. Pub. No. 2004/0229769 A1, published Nov. 18, 2005, to Smith et al., on paragraphs 26-31; or U.S. Pat. No. 6,494,920, at column 1, line 51 et seq. detailing an "esterquat" or a quaternized fatty acid triethanolamine ester salt.

In one embodiment, the FSA is chosen from at least one of the following: ditallowoyloxyethyl dimethyl ammonium chloride, dihydrogenated-tallowoyloxyethyl dimethyl ammonium chloride, ditallow dimethyl ammonium chloride, ditallowoyloxyethyl dimethyl ammonium methyl sulfate, dihydrogenated-tallowoyloxyethyl dimethyl ammonium chloride, dihydrogenated-tallowoyloxyethyl dimethyl ammonium chloride, or combinations thereof.

In one embodiment, the FSA may also include amide containing compound compositions. Examples of diamide comprising compounds may include but not limited to methyl-bis(tallowamidoethyl)-2-hydroxyethylammonium methyl sulfate (available from Degussa under the trade names Varisoft 110 and Varisoft 222). An example of an amide-ester containing compound is N-[3-(stearoylamino)propyl]-N-[2-(stearoyloxy)ethoxy)ethyl)]-N-methylamine.

Another specific embodiment of the invention provides for a rinse added fabric softening composition further comprising a cationic starch. Cationic starches are disclosed in US 2004/0204337 A1. In one embodiment, the rinse added fabric softening composition comprises from about 0.1% to about 7% of cationic starch by weight of the fabric softening composition. In one embodiment, the cationic starch is HCP401 from National Starch.

Suitable Laundry Care Ingredients

While not essential for the purposes of the present invention, the non-limiting list of laundry care ingredients illustrated hereinafter are suitable for use in the laundry care compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such ingredients are in addition to the components that were previously listed for any particular embodiment. The total amount of such adjuncts may range from about 0.1% to about 50%, or even from about 1% to about 30%, by weight of the laundry care composition.

The precise nature of these additional components, and levels of incorporation thereof, will depend on the physical form of the composition and the nature of the operation for which it is to be used. Suitable laundry care ingredients include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or coloring agents. In addition to the disclosure below, suitable examples of such other adjuncts and levels of use are found in U.S. Pat. Nos. 5,576,282, 6,306,812 B1 and 6,326,348 B1 that are incorporated by reference.

As stated, the laundry care ingredients are not essential to Applicants' laundry care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removaVanti-redeposition agents, brighteners, suds suppressors, dyes, additional perfumes and perfume delivery systems, structure elasticizing agents, fabric softeners, carriers, hydrotropes, processing aids and/or coloring agents. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexadecane. Suitable transition metal MRLs are readily prepared by known procedures, such as taught for example in WO 00/32601, and U.S. Pat. No. 6,225,464.

Exemplary Laundry Care Composition Formulations:
Liquid Detergent Formulations:
Table A provides examples of liquid detergent formulations which include at least one odor control molecule of the present invention.

TABLE A

Liquid Detergent Formulations Comprising the Present Odor Control Molecule

| Ingredient | 1a wt % | 1b wt % | 1c wt % | 1d wt % | 1e wt % | 1f[4] wt % |
|---|---|---|---|---|---|---|
| sodium alkyl ether sulfate | 14.4% | 14.4% | | 9.2% | 5.4% | |
| linear alkylbenzene sulfonic acid | 4.4% | 4.4% | 12.2% | 5.7% | 1.3% | 22.0% |
| alkyl ethoxylate | 2.2% | 2.2% | 8.8% | 8.1% | 3.4% | 18.0% |
| amine oxide | 0.7% | 0.7% | 1.5% | | | |
| citric acid | 2.0% | 2.0% | 3.4% | 1.9% | 1.0% | 1.6% |
| fatty acid | 3.0% | 3.0% | 8.3% | | | 16.0% |
| protease | 1.0% | 1.0% | 0.7% | 1.0% | | 2.5% |
| amylase | 0.2% | 0.2% | 0.2% | | | 0.3% |
| lipase | | | | 0.2% | | |
| borax | 1.5% | 1.5% | 2.4% | 2.9% | | |
| calcium and sodium formate | 0.2% | 0.2% | | | | |
| formic acid | | | | | | 1.1% |
| amine ethoxylate polymers | 1.8% | 1.8% | 2.1% | | | 3.2% |
| sodium polyacrylate | | | | | 0.2% | |
| sodium polyacrylate copolymer | | | | 0.6% | | |
| DTPA[1] | 0.1% | 0.1% | | | | 0.9% |
| DTPMP[2] | | | 0.3% | | | |
| EDTA[3] | | | | | 0.1% | |
| fluorescent whitening agent | 0.15% | 0.15% | 0.2% | 0.12% | 0.12% | 0.2% |
| ethanol | 2.5% | 2.5% | 1.4% | 1.5% | | |
| propanediol | 6.6% | 6.6% | 4.9% | 4.0% | | 15.7% |

TABLE A-continued

Liquid Detergent Formulations Comprising the Present Odor Control Molecule

| Ingredient | 1a wt % | 1b wt % | 1c wt % | 1d wt % | 1e wt % | 1f[4] wt % |
|---|---|---|---|---|---|---|
| sorbitol | | | | 4.0% | | |
| ethanolamine | 1.5% | 1.5% | 0.8% | 0.1% | | 11.0% |
| sodium hydroxide | 3.0% | 3.0% | 4.9% | 1.9% | 1.0% | |
| sodium cumene sulfonate | | | 2.0% | | | |
| silicone suds suppressor | | | 0.01% | | | |
| perfume | 0.3% | 0.3% | 0.7% | 0.3% | 0.4% | 0.6% |
| Odor Control Molecule | 0.013% | 0.001% | 0.005% | 0.003% | 0.0005% | 0.001% |
| water | balance | balance | balance | balance | balance | balance |
| | 100.0% | 100.0% | 100.0% | 100.0% | 100.0% | 100.0% |

[1] diethylenetriaminepentaacetic acid, sodium salt
[2] diethylenetriaminepentakismethylenephosphonic acid, sodium salt
[3] ethylenediaminetetraacetic acid, sodium salt
[4] a compact formula, packaged as a unitized dose in polyvinyl alcohol film Granular Detergent Formulations:
Table B provides examples of granular detergent formulations which include at least one odor control molecule of the present invention.

TABLE B

Granular Detergent Formulations Comprising the Present Odor Control Molecule

| Ingredient | 2a wt % | 2b wt % | 2c wt % | 2d wt % | 2e wt % |
|---|---|---|---|---|---|
| Na linear alkylbenzene sulfonate | 3.4% | 3.3% | 11.0% | 3.4% | 3.3% |
| Na alkylsulfate | 4.0% | 4.1% | | 4.0% | 4.1% |
| Na alkyl sulfate (branched) | 9.4% | 9.6% | | 9.4% | 9.6% |
| alkyl ethoxylate | | | 3.5% | | |
| type A zeolite | 37.4% | 35.4% | 26.8% | 37.4% | 35.4% |
| sodium carbonate | 22.3% | 22.5% | 35.9% | 22.3% | 22.5% |
| sodium sulfate | 1.0% | | 18.8% | 1.0% | |
| sodium silicate | | | 2.2% | | |
| protease | 0.1% | 0.2% | | 0.1% | 0.2% |
| sodium polyacrylate | 1.0% | 1.2% | 0.7% | 1.0% | 1.2% |
| carboxymethylcellulose | | | 0.1% | | |
| PEG 600 | | 0.5% | | | 0.5% |
| PEG 4000 | | 2.2% | | | 2.2% |
| DTPA | 0.7% | 0.6% | | 0.7% | 0.6% |
| fluorescent whitening agent | 0.1% | 0.1% | 0.1% | 0.1% | 0.1% |
| sodium percarbonate | | 5.0% | | | 5.0% |
| sodium nonanoyloxybenzenesulfonate | | 5.3% | | | 5.3% |
| silicone suds suppressor | 0.02% | 0.02% | | 0.02% | 0.02% |
| perfume | 0.3% | 0.3% | 0.2% | 0.3% | 0.3% |
| Odor Control Molecule | 0.004% | 0.006% | 0.002% | 0.004% | 0.02% |
| water and miscellaneous | balance | balance | balance | balance | balance |
| | 100.0% | 100.0% | 100.0% | 100.0% | 100.0% |

Fabric Treatment Compositions:
Table C provides examples of liquid fabric treatment compositions which include at least one odor control molecule of the present invention.

TABLE C

Liquid Fabric Treatment Compositions Comprising the Present Odor Control Molecule

| Ingredients | a | b | c | d |
|---|---|---|---|---|
| Fabric Softening Active[a] | 13.70% | 13.70% | 13.70% | 13.70% |
| Ethanol | 2.14% | 2.14% | 2.14% | 2.14% |
| Cationic Starch[b] | 2.17% | 2.17% | 2.17% | 2.17% |
| Perfume | 1.45% | 1.45% | 1.45% | 1.45% |
| Phase Stabilizing Polymer[c] | 0.21% | 0.21% | 0.21% | 0.21% |
| Calcium Chloride | 0.147% | 0.147% | 0.147% | 0.147% |
| DTPA[d] | 0.007% | 0.007% | 0.007% | 0.007% |
| Preservative[e] | 5 ppm | 5 ppm | 5 ppm | 5 ppm |
| Antifoam[f] | 0.015% | 0.015% | 0.015% | 0.015% |
| Odor Control Molecule | 30 ppm | 30 ppm | 30 ppm | 15 ppm |
| Tinopal CBS-X[g] | 0.2 | 0.2 | 0.2 | 0.2 |
| Ethoquad C/25[h] | 0.26 | 0.26 | 0.26 | 0.26 |

TABLE C-continued

Liquid Fabric Treatment Compositions Comprising the Present Odor Control Molecule

| Ingredients | a | b | c | d |
|---|---|---|---|---|
| Ammonium Chloride | 0.1% | 0.1% | 0.1% | 0.1% |
| Hydrochloric Acid | 0.012% | 0.012% | 0.012% | 0.012% |
| Deionized Water | Balance | Balance | Balance | Balance |

$^a$N,N-di(tallowoyloxyethyl)-N,N-dimethylammonium chloride.
$^b$Cationic starch based on common maize starch or potato starch, containing 25% to 95% amylose and a degree of substitution of from 0.02 to 0.09, and having a viscosity measured as Water Fluidity having a value from 50 to 84.
$^c$Copolymer of ethylene oxide and terephthalate having the formula described in U.S. Pat. No. 5,574,179 at col.15, lines 1-5, wherein each X is methyl, each n is 40, u is 4, each $R^1$ is essentially 1,4-phenylene moieties, each $R^2$ is essentially ethylene, 1,2-propylene moieties, or mixtures thereof.
$^d$Diethylenetriaminepentaacetic acid.
$^e$KATHON® CG available from Rohm and Haas Co.
$^f$Silicone antifoam agent available from Dow Corning Corp. under the trade name DC2310.
$^g$Disodium 4,4'-bis-(2-sulfostyryl) biphenyl, available from Ciba Specialty Chemicals.
$^h$Cocomethyl ethoxylated [15] ammonium chloride, available from Akzo Nobel.

The odor control molecule may be incorporated into a spray or aerosol. The spray may include additional ingredients which allow the odor control molecule to be released from a spray container (such as a pump spray bottle). Similarly, if the odor control molecule is provided in an aerosol, additional ingredients (such as aerosol propellants), may be incorporated in an aerosol container (such as an aerosol can).

The odor control molecule of the present invention may be included in a floorcovering cleaning composition. The floorcovering cleaning composition is used to remove unwanted material (such as dirt, soil, stains, and the like) from a floorcovering article. The term "floorcovering article," as used herein, is intended to describe a textile substrate which comprises face fibers and which is utilized to cover surfaces on which people are prone to walk. Thus, carpets (broadloom, tile, or otherwise) and floor mats (outdoor, indoor, and the like) are specific types of floorcovering articles.

In one exemplary multi-layered floorcovering article, the article is made up of a primary textile substrate formed from a plurality of pile yarns tufted through a primary backing layer such as a scrim or nonwoven fibrous material of polyester or polypropylene as will be well known to those skilled in the art. A precoat backing layer of a resilient adhesive such as styrene butadiene rubber latex may be disposed across the underside of the primary textile substrate so as to hold the pile yarns in place within the primary backing layer. An adhesive layer, such as a hot melt adhesive, may be included and extends away from the precoat backing layer. A layer of stabilizing material such as woven or nonwoven glass may be disposed at a position between the adhesive layer and a cushioning layer such as virgin or rebounded polyurethane foam or the like. A secondary backing layer such as a nonwoven blend of polyester and polypropylene fibers may be disposed across the underside of the cushioning layer.

As will be appreciated, the actual construction of the multi-layered floorcovering article may be subject to a wide range of variations. Accordingly, the multi-layered construction described herein is to be understood as constituting merely an exemplary construction representative of a floorcovering article and that the present odor control molecule is equally applicable to any other construction of carpets and/or floor mats as may be desired. By way of example only, various carpet tile constructions are described in U.S. Pat. Nos. 6,203,881 and 6,468,623. Various floor mat constructions are described, for example, in US Patent Application Publication Nos. 2017-0037567 A1, 2017-0037568 A1, and 2018-0056626 A1.

In the event that the substrate structure is a carpet, the pile yarns may be either spun or filament yarns formed of natural fibers such as wool, cotton, or the like. The pile yarns may also be formed of synthetic materials such as polyamide polymers including nylon 6 or nylon 6,6; polyesters such as PET and PBT; polyolefins such as polyethylene and polypropylene; rayon; and polyvinyl polymers such as polyacrylonitrile. Blends of natural and synthetic fibers such as blends of cotton, wool, polyester and nylon may also be used within the pile yarns. Pile yarns may be present in a loop pile construction. Of course, it is to be understood that other pile constructions as will be known to those of skill in the art including cut pile constructions and the like may likewise be used.

Floorcovering cleaning compositions contain at least one floorcovering cleaning ingredient. Floorcovering cleaning ingredients include, without limitation, one or more of the following: organic liquids, surfactants, surface active agents, static reducing additives, dust suppressing additives, vacuum retrieval additives, absorbent particulate material, super absorbent polymers, metal ion chelators, stain resist agents, pH adjusters, fragrance, biocides, water, and the like. The floorcovering cleaning composition containing at least one odor control molecule of the present invention may be provided in any form (e.g. solid, semi-solid, liquid) that allows for application to a floorcovering article. Application may occur, for example, by spraying or sprinkling the composition onto the surface of a floorcovering article. Application may be followed by agitation and then optionally by removal.

Additionally, it is contemplated that the odor control molecule of the current invention may be ideal for use in thermoset materials (such as, for example, polyurethane foam). Examples of specific thermoset formulations, which may be suitable for use with the odor control molecule of the present invention, are disclosed in commonly assigned U.S. Pat. No. 4,284,729 to Cross et al. and U.S. Pat. No. 4,846,846 to Rekers et al. In general, polyurethane foam is produced through the catalyzed polymerization of the reaction products of polyols and isocyanates. Blowing agents present within the polymerization step typically provide the necessary foam-making capability. Such a reaction is well known throughout the polyurethane industry and has been practiced for many years.

Thus, further contemplated to be within the scope of the present invention is a thermoset material containing the odor control molecule as described herein. In one aspect of the invention, the thermoset material is a polyurethane foam material. Polyurethanes are typically made by reacting isocyanate with active hydrogen-containing compounds. The polyurethane polymer is then expanded (or "blown") to create a polyurethane foam material via the introduction of bubbles and a gas. Thus, the present invention includes a polyurethane foam material that contains at least one polyurethane foam ingredient and the odor control molecule described herein. Polyurethane foam ingredients include, without limitation, one or more of the following: polyols, isocyanates, catalysts, silicones, antioxidants (such as phenols and hindered phenols), ultraviolent absorbing agents, blowing agents (such as carbon dioxide released from reaction of isocyanate with water), organic liquids, coloring agents (including dyes, pigments, polymeric colorants, and the like, and mixtures thereof), biocides, water, and the like.

Suitable polyols utilized within this invention include those comprising at least two alcohol moieties, preferably at least three. The free hydroxyl groups react well with the isocyanates to form the urethane components which are then polymerized to form the desired polyurethanes. Blowing agents present within the polymerization step provide the necessary foam-making capability. Preferred polyols thus comprise between three and six alcohol moieties, comprising from between one and six carbon atoms per alcohol moiety. In one aspect of the invention, a typical trifunctional polyol is utilized (such as 3022 polyol, available from Bayer).

Isocyanates, such as diisocyanates, are well known components of such polyurethane foams and include any compounds which possess at least one free cyanate reactive group, and most preferably two, although more may be utilized. Such compounds are may also be aliphatic or aromatic in nature. The most prominently utilized isocyanates are toluene diisocyanate and methylene diisocyanate. The polyol is generally reacted with a slight excess of isocyanate (ratio of from 1:1.04 to 1:1.12) to produce a soft foam product; the greater the ratio, the harder the foam thus produced). In practice, two separate streams of liquids (one of polyol, the other of isocyanate) are mixed together in the presence of a polymerization catalyst and a blowing agent in order to produce the desired polyurethane foam product.

The catalyst used for foam production encompasses any type that effectuates the polymerization of the isocyanate/polyol reactants noted above to form the desired polyurethane in foam form. The term "tertiary amine-based hydroxy-containing catalyst" is intended to encompass any gelation/blowing catalyst utilized within polyurethane production which comprises at least one amine constituent. Amine-based catalysts, and more specifically, tertiary amine catalysts, are widely utilized within such specific foam-producing methods.

Other additives or solvents may also be present within the foam-making composition. Auxiliary blowing agents are required to provide the necessary foam blowing capability and reduce chances of combustion. Such compounds include methylene chloride, acetone, carbon dioxide (which may be liberated during the reaction between water and isocyanate), and the like, and are present in amounts of between about 1.0 parts per hundred parts polyol (also referred to herein as "php") and 10 php of the entire foam-making composition. Water may thus also be added in relatively low amount (i.e., from about 3 to about 10 php; most preferably between about 3 and 7 php) to provide carbon dioxide for blowing purposes. Silicones may be added to provide desired cell structure and foam stability and are present in an amount from about 0.1 to about 2 php of the entire foam-making composition; preferably from about 0.9 to about 1.6 php.

An odor control composition of the present invention may be comprised of at least one odor control molecule as described herein and at least one solvent. Solvents include, for example and without limitation, water, hydrocarbons (such as mineral oil), perchloroethylene, carbon tetrachloride, acetone, alcohol and the like. Further suitable solvents include $C_{4-14}$ ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-$C_5$ alcohols, linear $C_1$-$C_5$ alcohols, amines, $C_8$-$C_{14}$ alkyl and cycloalkyl hydrocarbons and halohydrocarbons, and mixtures thereof. Additional solvents suitable for use in the present invention include those listed by the American Chemical Society, Division of Organic Chemistry, "Common Organic Solvents: Table of Properties," which is located at https//www.organicdivision.org/orig/organic_solvents.html. Any combination of the aforementioned solvents may be utilized.

EXAMPLES

The following examples further illustrate the subject matter described above but, of course, should not be construed as in any way limiting the scope thereof.

The substituted polyethyleneimine compound was synthesized and tested for its deposition during the wash cycle at several concentrations in laundry detergent and fabric softening compositions. The washings were carried out for cotton and polyester-containing fabrics. Detailed synthesis and testing results are reported below in more detail.

Example 1

A substituted polyethyleneimine compound was made according to the procedure described below. For reference, an idealized reaction scheme is also shown below:

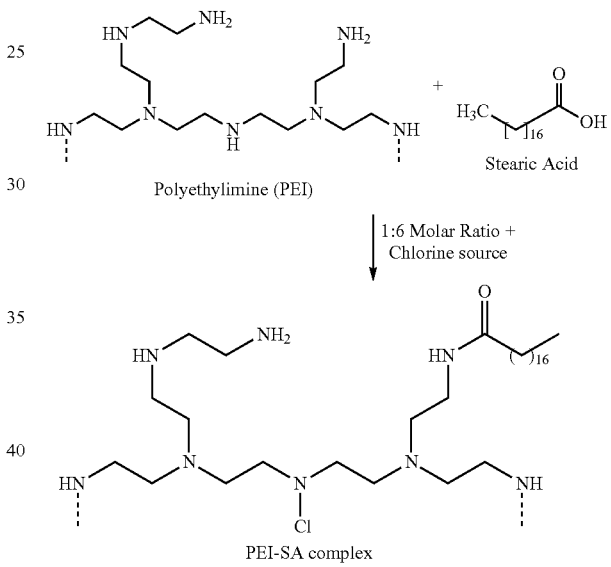

The substituted polyethyleneimine compound contained a PEI to stearic acid molar ratio of 1:6. The complex was made according to the procedure described below.

The following materials were used to prepare the substituted polyethyleneimine compound:

| Material | Target Amount (g) | Actual Amount (g) |
|---|---|---|
| Lupasol® WF (PEI with MW = 25000) | 26.6 | 27.0 |
| Stearic Acid | 1.88 | 1.9 |
| Chlorinated Tap Water | 139.22 | 139.2 |

1. Lupasol®WF was warmed at 80° C. for 1 hour. The warmed Lupasol®WF was then added to a round bottom flask and heated to 82° C. with stirring. The 82° C. temperature was maintained.
2. Stearic acid was slowly added to the warm PEI. The mixture was stirred at 82° C. for 30 minutes.

3. The mixture was then heated to 138° C. and held for 2 hours. Sample was checked with IR spectroscopy to determine if reaction was complete.
4. The mixture was then cooled to 82° C.
5. Chlorinated tap water, obtained from the faucet in the laboratory, was then added to a vessel and heated to 82° C.
6. The warm tap water was then added to the substituted polyethyleneimine compound mixture of step #4.
7. The mixture was stirred for 30 minutes and then cooled to 43° C.
8. Another IR test was conducted to check that the acids completely reacted with the amines.
9. The pH was checked and was in the range from 10 to 11.
10. Percent solids were calculated to be 16.82.

Comparative Example 1

Comparative Example 1 was made according to the procedure described for Example 1, except tap water was replaced with deionized ("DI") water. Percent solids were calculated to be 16.76.

Example 2

Example 2 was made by taking 15 grams of the Example 1 material and adjusting the pH to 7 with 1.581 grams of glacial acetic acid. Percent solids was calculated to be about 20%.

Comparative Example 2

Comparative Example 2 was made according to the procedure described for Example 2, except tap water was replaced with deionized ("DI") water. The pH was adjusted to 7 by adding acetic acid. Percent solids was calculated to be about 20%.

Milk Test Procedure:

The test was carried out as follows:

Cotton and polyester fabric samples were cut into 1.5" diameter discs and stacked with a 2-ply thickness. Each disc stack was placed into a sterile petri dish and exposed to 0.5 mL of 2% milk using a pipettor. Using forceps, the disc stacks were removed from the petri dish and placed in a 4 oz. glass jar. The lid was tightened on the jar and placed in an incubator at 37° C. for 2 days. After 2 days, the jars were removed from the incubator and evaluated for odor.

Odor generated by the milk on the treated samples was evaluated by objectively smelling each sample. In some testing one of the following descriptive terms was used to evaluate odor: very bad smell, smell, less smell, no smell. If the sample exhibits very bad smell, then it indicates that the odor control molecule is not very effective. If the sample exhibits less smell, then it indicates that the odor control molecule works to reduce the amount of odor generated from the test. If the sample exhibits no smell, then the odor control molecule works to eliminate any odor that may have been generated from the test.

In other testing, some samples were evaluated by using a numerical scale from 1 to 3. A "1" rating indicated that the sample in the jar had an offensive odor. A "2" rating indicated that the sample in the jar was beginning to smell bad. A "3" rating indicated that no odor was present, or a warm milk smell was present.

Acid Test Procedure:

Headspace Gas Chromatography ("GC") was used to analyze the volatile organic acids that were neutralized by the treated fabric versus the untreated fabric. This was a solid phase micro extraction method.

Washing Procedure:

The following wash procedure was used to evaluate odor control molecule deposition on treated fabrics and their ability to control odor.

Application—Laundry
Base Description—AATCC 2003 Standard Reference Liquid Detergent Without Optical Brighteners
Washing Method—Tergotometer
Wash Temperature—25° C.
Fabric to Water Ratio—40 g of fabric to 1 liter water
Wash directions—Add 0.5 g of detergent to 500 mL of water and mix for 1 minute at 200 rpm. Add 20 g of fabric. Stir for 15 minutes
Rinse directions—Squeeze water out of fabrics. Place 500 mL of cold water in beaker and stir by hand. Squeeze water out of fabrics and repeat.
Drying method/time—Tumble dry for 1 hour.

Chloramine Analysis Procedure:

Literature teaches that the presence of N—Cl groups (i.e. chloramines) in a compound or composition can be determined using a titration technique that provides a visual color change for samples containing N—Cl groups. See, for instance, "Current Technology of Chlorine Analysis for Water and Wastewater," Technical Information Series—Booklet No. 17 by Daniel L. Harp. Hach Company, 2002. Samples containing N—Cl groups will exhibit a pink hue. No color change is observed for samples that are free from N—Cl groups (the solution will remain colorless). Samples were evaluated for the presence of N—Cl groups using the following procedure:

1. In a container, 10 mL of tap water was added to each sample being evaluated.
2. The container was stirred.
3. The container was heated to 100° C. and maintained until all the water was boiled off and only dried material remained in the container.
4. DPD chlorine reagent (from the DPD test kit) and 10 mL of deionized water was added to the dried powder.
5. The mixture was stirred.
6. The sample was then observed for color change.
7. Steps 1-6 were repeated with a fresh sample, except that tap water in step #1 was replaced with deionized water.

Each sample was visually observed for color change. Samples that did not contain N—Cl groups remained colorless. Samples that contained N—Cl groups exhibited a pink color within a few minutes of time (e.g. 2 to 8 minutes or 4 to 6 minutes).

Additional evaluation was conducted using a UV-Visible Spectrophotometer to determine the absorbance peak of each sample. Samples containing N—Cl groups exhibited an absorbance peak around 250 nm to 300 nm, while samples that did not contain N—Cl groups did not exhibit an absorbance peak.

Each Example and Comparative Example was tested for odor control by exposing 100% cotton fabric treated with the odor control molecules to an internally created milk test (SPI MBSPI16) and acid test. The amount of each sample deposited on the cotton fabrics and the test results are shown in Table 1. "Force Deposit" indicates that the complex was added by knife coating the complex onto the fabric. "Wash" indicates that the complex was added as a liquid to a beaker with the fabric and agitated. "Rinse" indicates that the complex was added by repeated exposure (3 times) to DI water and squeezed out each time. "NA" indicates that the test parameter was not applicable to a particular sample.

TABLE 1

Odor Control on Cotton Fabric

| Sample | Force Deposit | Wash | Rinse | Milk Test Results | Acid Test Results |
|---|---|---|---|---|---|
| Control | NA | NA | NA | Very bad smell | NA |
| Example 1 | 8% | NA | NA | No smell | NA |
| Example 2 | 7-8% | NA | NA | No smell | NA |
| Comparative Example 1 | 7-8% | NA | NA | Less smell | NA |
| Comparative Example 2 | 7-8% | NA | NA | Less smell | NA |
| Example 1 | NA | 10% solution | 4% wt. deposit | No smell | NA |
| Example 1 | NA | 5% solution | 2% wt. deposit | No smell | NA |
| Example 1 | NA | 1% solution | Deposited in error | Smell | NA |
| Example 1 | NA | 10% solution | 4% wt. deposit | NA | No smell |
| Example 1 | NA | 5% solution | 2% wt. deposit | NA | No smell |
| Control | NA | NA | NA | NA | Smell |

The test results demonstrate that the halogen-containing substituted polyethyleneimine compounds (tap water samples) exhibited better odor control results than the substituted polyethyleneimine compounds without halogen (de-ionized water samples). The milk samples were also evaluated on a numerical scale. The Control sample was evaluated as a 3. Example 1 was evaluated as a 1.0, and Comparative Example 1, Example 2, and Comparative Example 2 were all evaluated as a 1.5.

Further tests were conducted in order to determine odor control of the molecule for cotton and polyester fabrics after washing. Test results are shown in Table 2.

TABLE 2

Odor Control on Cotton Fabric After Washing

| Sample | Wash Conditions | Dry | Milk Test | Acid/Sweat Test |
|---|---|---|---|---|
| Control | AATCC | NA | Very bad smell | NA |
| Example 1 | AATCC + 1.2 ppm in wash water | Dried | Very bad smell | NA |
| Example 1 | AATCC + 2.4 ppm in wash water | Dried | Less smell | NA |
| Example 1 | AATCC + 6 ppm in wash water | Dried | No smell | NA |
| Example 1 | AATCC | Dried | NA | Acid smell |
| Example 1 | AATCC + 6 ppm in wash water | Dried | NA | No smell |
| Example 1 | 2% by wt. deposit | Dried | NA | No smell |
| Example 1 | AATCC | Dried | NA | Sweet fruity smell |
| Example 1 | AATCC + 6 ppm in wash water | Dried | NA | Less smell |
| Example 1 | 2% by wt. deposit | Dried | NA | No smell |

Test results indicate that the N-halamine-containing PEI-steric complex odor control molecule of the present invention (Example 1) with 6 ppm loadings in wash water for cotton provided much better odor control for the milk test compared to the control samples. Similarly, the odor control complex of the present invention (Example 1) provided much better odor control for the acid and sweat tests compared to the control samples. These tests were also repeated with 5, 10, and 100 ppm samples of the odor control molecule (Example 1) in wash water and in for 3 different test batches. Each time, the samples with 5 or 10 ppm loadings provided much better odor control compared to control samples. Without being bound by theory, it is believed that acetic acid gets trapped in the odor control molecule as a result of the proton transfer mechanism described herein previously.

Similar trends were observed on polyester fabric. The presence of the odor control molecule of the present invention in amounts in the range from about 1 ppm to about 100 ppm in wash water, or even 2 ppm to about 50 ppm, or even 5 ppm to about 10 ppm was effective in controlling odor compared to control samples. Additionally, similar test results were obtained for butyric acid and artificial sweat.

Additional odor control testing was done by adding 0.5% of the active odor control molecule to each of the following laundry care compositions: Tide® Coldwater Clean liquid laundry detergent, Gain® Original liquid laundry detergent, and Ultra Downy® Free & Gentle liquid fabric softener. The samples were then washed using the laundry care compositions containing the odor control molecule. Cotton and polyester fabric samples were exposed to the milk test as herein before described. In every instance, the laundry care composition containing the odor control molecule exhibited improved odor control (and fabric whiteness upon visual inspection) when compared to a control sample that did not contain the odor control molecule.

Further testing was conducted in order to evaluate the molar ratio of PEI (MW=25,000) to stearic acid with respect to odor control. All samples were prepared at about pH=10. Test results are provided in Table 3.

TABLE 3

Effect of PEI (MW = 25000) to Stearic Acid Molar Ratio on Odor Control

| Sample | Fabric Treated | Ratio of PEI to Stearic Acid | Amount of Odor Control Complex Added to Wash Water (ppm) | Milk Test Result |
|---|---|---|---|---|
| Cotton Control | Cotton | NA | 0 | 1 |
| PET Control | Polyester | NA | 0 | 2 |
| Example 3 | Cotton | 1:5 | 5 | 2 |
| Example 1 | Cotton | 1:6 | 5 | 3 |
| Example 4 | Cotton | 1:7 | 5 | 3 |
| Example 5 | Cotton | 1:9 | 5 | 2 |
| Example 3 | Cotton | 1:5 | 10 | 2 |
| Example 1 | Cotton | 1:6 | 10 | 3 |
| Example 4 | Cotton | 1:7 | 10 | 3 |
| Example 5 | Cotton | 1:9 | 10 | 2 |
| Example 3 | Polyester | 1:5 | 5 | 2 |
| Example 1 | Polyester | 1:6 | 5 | 3 |
| Example 4 | Polyester | 1:7 | 5 | 3 |
| Example 5 | Polyester | 1:9 | 5 | 2 |
| Example 3 | Polyester | 1:5 | 10 | 2 |
| Example 1 | Polyester | 1:6 | 10 | 3 |
| Example 4 | Polyester | 1:7 | 10 | 3 |
| Example 5 | Polyester | 1:9 | 10 | 2 |

Additional testing was conducted in order to evaluate the molar ratio of PEI to stearic acid with respect to odor control at various molecular weights of the PEI. Test results are provided in Table 4.

TABLE 4

Effect of PEI to Stearic Acid Molar Ratio on Odor Control at Various PEI Molecular Weights

| Sample | PEI Molecular Weight | Fabric Treated | Ratio of PEI to Stearic Acid | Amount of Odor Control Complex Added to Wash Water (ppm) | Milk Test Result |
|---|---|---|---|---|---|
| Cotton Control | NA | Cotton | NA | 0 | 1 |
| PET Control | NA | Polyester | NA | 0 | 2 |
| Example 6 | 10,000 | Cotton | 1:2 | 5 | 2 |
| Example 7 | 10,000 | Cotton | 1:3 | 5 | 3 |
| Example 8 | 10,000 | Cotton | 1:4 | 5 | 1 |
| Example 6 | 10,000 | Cotton | 1:2 | 10 | 2 |
| Example 7 | 10,000 | Cotton | 1:3 | 10 | 3 |
| Example 8 | 10,000 | Cotton | 1:4 | 10 | 1 |
| Example 6 | 10,000 | Polyester | 1:2 | 5 | 2 |
| Example 7 | 10,000 | Polyester | 1:3 | 5 | 3 |
| Example 8 | 10,000 | Polyester | 1:4 | 5 | 1 |
| Example 6 | 10,000 | Polyester | 1:2 | 10 | 2 |
| Example 7 | 10,000 | Polyester | 1:3 | 10 | 3 |
| Example 8 | 10,000 | Polyester | 1:4 | 10 | 1 |
| Example 9 | 2000 | Cotton | 1:1 | 5 | 3 |
| Example 10 | 2000 | Cotton | 1:2 | 5 | 1 |
| Example 9 | 2000 | Cotton | 1:1 | 10 | 3 |
| Example 10 | 2000 | Cotton | 1:2 | 10 | 1 |
| Example 9 | 2000 | Polyester | 1:1 | 5 | 3 |
| Example 10 | 2000 | Polyester | 1:2 | 5 | 1 |
| Example 9 | 2000 | Polyester | 1:1 | 10 | 3 |
| Example 10 | 2000 | Polyester | 1:2 | 10 | 1 |

Quantitative analysis using headspace GC for the samples in Table 4 was also conducted. Fabric treated with the odor control molecule of the present invention exhibited good odor control compared to the control samples. Specifically, GC testing showed no peaks for volatile organic acids (i.e. small chain fatty acids that cause odor, such as butyric acid, valeric acid and isovaleric acid) on the treated fabric. However, GC testing of the control (untreated) samples showed peaks for the same volatile organic acids (i.e. small chain fatty acids that cause odor, such as butyric acid, valeric acid and isovaleric acid). Thus, fabrics treated with the odor control molecule of the present invention exhibited much better absorption of the acids leading to odor compared to the control samples.

Further testing was conducted in order to evaluate the presence of halogen atoms (e.g. chlorine) in the PEI-stearic acid complex and its effect on odor control. Test results are provided in Table 5.

The following materials and procedures were used to prepare the substituted polyethyleneimine compound:

| Material | Raw Materials | Mass (g) | Purity | Molecular Weight (MW) | mol | Equivalent |
|---|---|---|---|---|---|---|
| 1 | Lupasol ® FT WF | 50 | 1 | 25000 | 0.00200 | 1 |
| 2 | Stearic Acid | 3.41 | 1.00 | 284.3 | 0.01200 | 6 |
| 3 | DI water | 100.00 | | | | |

1. Lupasol® FT WF was warmed in an oven at 70-80° C. The warmed Lupasol® FT WF was then added to a round bottom flask and heated to 82° C.
2. Stearic acid was slowly added to the warm PEI. Care was taken to avoid potential foaming due to acid base reaction.
3. The mixture was then heated to 138° C. and held for 2.5 hours. Sample was checked with IR spectroscopy to determine if reaction was complete.
4. The mixture was then cooled to 70° C.
5. Hot DI water was added to raise temperature to 82° C.
6. The mixture was then left overnight.
7. The next day, the mixture was stirred for 30 minutes at 80-90° C.
8. The mixture was poured into a container.

Four samples of 10 g each were removed from the container and placed into four separate vials. The following was added to each sample:
   a. 80 mg sodium hypochlorite (13% aq., 1 equivalent)
   b. 160 mg sodium hypochlorite (13% aq., 2 equivalent)
   c. 240 mg sodium hypochlorite (13% aq., 3 equivalent)
   d. 320 mg sodium hypochlorite (13% aq., 4 equivalent)
Each sample was mixed on the sonicator or vortex to distribute the sodium hypochlorite material. The pH was in the range from 9 to 10.

TABLE 5

Effect of Chlorine in PEI-Stearic Acid Complex on Odor Control

| Sample | Number of Chlorine Equivalents | Fabric Treated | Ratio of PEI (MW = 25000) to Stearic Acid | Amount of Odor Control Complex Added to Wash Water (ppm) | Milk Test Result |
|---|---|---|---|---|---|
| Example 1 | 1:1 | Cotton | 1:6 | 5 | 2 |
| Example 11 | 1:2 | Cotton | 1:6 | 5 | 3 |
| Example 12 | 1:3 | Cotton | 1:6 | 5 | 3 |
| Example 13 | 1:4 | Cotton | 1:6 | 5 | 1 |
| Example 1 | 1:1 | Polyester | 1:6 | 5 | 1 |
| Example 11 | 1:2 | Polyester | 1:6 | 5 | 3 |
| Example 12 | 1:3 | Polyester | 1:6 | 5 | 3 |
| Example 13 | 1:4 | Polyester | 1:6 | 5 | 1 |

Another test was conducted to independently evaluate myristic acid and capric acid as the electrophilic compound reacted with the PEI molecule (MW=2000) with a halogenating agent (NaOCl). Myristic acid gave good results with polyester fabric at 1:1 ratio, while capric acid gave good results with 1:2 ratio.

A further test was conducted using PEI (MW=2000) and two halogenating agents without an acid source. PEI was first reacted with dodecyl chloride. The 1:1 ratio of the reaction was then treated with 1 equivalents of NaOCl. The product gave very good results on odor control. An idealized structure that was produced is shown below:

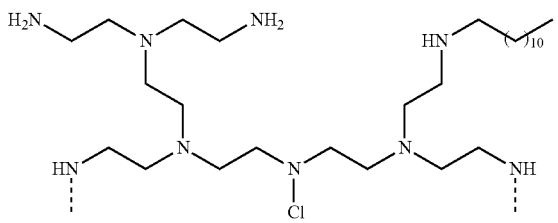

Further testing was done to evaluate other amounts of the substituted polyethyleneimine compound in a laundry care composition. Example 14 was created by adding 0.5 wt % of Example 1 to Tide® liquid laundry detergent. Example 15 was created by adding 0.5 wt % of Example 1 to Gain® liquid laundry detergent. Example 16 was created by adding 0.5 wt % of Example 1 to Downy® liquid fabric softener.

Textile substrates were laundered/treated according to methods described herein. The solutions were evaluated after 10 days at room temperature, after 28 days at room temperature, and after 28 days at 50° C. Once the fabric was washed, it was tested for odor control using the milk test procedure. Under all testing environments, the treated textile substrates exhibited good odor control and always better odor control than each of the control samples (detergent and/or fabric softener without the odor control molecule).

It was also observed that each of the control samples exhibited a yellowish and/or brownish color after the milk test procedure. However, each of the inventive samples (Examples 14, 15 and 16) maintained a white appearance with no discoloration.

Similar odor control and non-discoloration results for Examples 14, 15 and 16 were also observed when added to powder AATCC laundry detergents instead of the Tide® and Gain® liquid laundry detergents.

Additional testing was done to evaluate the combination of the odor control molecule of the present invention with other odor controlling compounds. Example 14 was created by combining 2.5 ppm of Example 1 with 2.5 ppm of chitosan. Example 15 was created by combining 2.5 ppm of Example 1 with 2.5 ppm of cyclodextrin. Each of Example 14 and Example 15 was added to liquid laundry detergent. Textile substrates were laundered according to methods described herein. The treated substrates were then tested according to the milk test described herein. The treated textile substrates exhibited good odor control.

Polyurethane Foam Example A

A standard colored polyurethane foam article was made similar to the process disclosed in U.S. Pat. No. 4,846,846 to Rekers et al. The components employed in the foam formulation were as follows (php=parts per hundred parts polyol):

| Component | Amount |
|---|---|
| F3022 Polyol | 100 parts |
| Water | 4.53 php |
| DABCO TL (catalyst, available from Air Products) | 0.15 php |
| DABCO T10 (catalyst, available from Air Products) | 0.30 php |
| L520 Silicone (from Witco) | 1.0 php |
| 80/20 toluene diisocyanate* | 43.6 php |
| Coloring Agent** | 1.0 php |
| Inventive Odor Control Molecule | 1-4 php (or 0.1% to 0.5% by weight of foam) |

*The 80/20 toluene diisocyanate is a mixture of isomers containing 80% 2,4-toluene diisocyanate and 20% 2,6-toluene diisocyanate.
**The Coloring Agent consisted of at least one Reactint® colorant (such as Reactint® Yellow X15 and/or Reactint® Blue X3LV), available from Milliken & Company of Spartanburg, South Carolina. Reactint® polymeric colorants are liquid polymeric colorants useful for coloring polyurethane and other thermoset resins. These colorants are reactive polymeric colorants that consist of chromophores which are chemically bound to polyols. This arrangement allows the polymeric colorant to react into the polyurethane polymer matrix. Unlike pigment pastes, which are dispersions of solid particles in a liquid carrier, Reactint® polymeric colorants are 100% homogeneous liquids that are soluble in polyol and will not settle over time. Because of this pure liquid and easy to disperse nature, it is possible to blend Reactint® colorants in-line and on-the-fly, while producing polyurethane foams and resins.

The components above were combined and mixed together within a reaction vessel, the reaction created a "health" bubble (indicating gelation and blowing balance), and the vessel was then exposed to 185° C. (generated within a microwave oven to simulate actual heat history encountered on an industrial production level) for about 10 minutes. A polyurethane foam article containing the odor control molecule of the present invention was thus produced.

Polyurethane Foam Example B

A polyurethane foam article was produced. Such a foam was produced through the reaction of the following components:

| Component | Amount |
|---|---|
| F3022 Polyol | 100 parts |
| Water | 4.53 php |
| DABCO TL (catalyst) | 0.15 php |
| DABCO T10 (catalyst) | 0.30 php |
| L520 Silicone (from Witco) | 1.0 php |
| 80/20 toluene diisocyanate | 43.6 php |
| Coloring Agent* | 1.0 php |
| Inventive Odor Control Molecule | 1-4 php (or 0.1% to 0.5% by weight of foam) |

*The Coloring Agent consisted of at least one Reactint® colorant (such as Reactint® Yellow X15 and/or Reactint® Blue X3LV), available from Milliken & Company of Spartanburg, South Carolina.

Upon mixture within a reaction vessel, the reaction created a "health" bubble (indicating gelation and blowing balance), and the vessel was then exposed to 185° C. (generated within a microwave oven to simulate actual heat history encountered on an industrial production level) for about 10 minutes. A polyurethane foam article containing the odor control molecule of the present invention was thus produced.

Polyurethane Foam Example C

A polyurethane foam article was produced. Such a foam was produced through the reaction of the following components:

| Component | Amount |
| --- | --- |
| F3022 Polyol (from Bayer) | 100 grams |
| Water | 4.53 ml |
| DABCO 33LV (catalyst, from Air Products) | 0.15 ml |
| DABCO T10 (catalyst) | 0.32 ml |
| L520 Silicone (from Crompton) | 1.0 mL |
| 80/20 Toluene diisocyanate (Bayer, 112 index) | 49.0 ml |
| Reactint ® Blue X3LV | 1.0 php |
| Antioxidant (Tinuvin ® 326) | 1.5 php |
| Inventive Odor Control Molecule | 1-4 php (or 0.1% to 0.5% by weight of foam) |

Upon mixture within a reaction vessel, the reaction created a "health" bubble (indicating gelation and blowing balance), and the vessel was then exposed to 160° C. (generated within a conventional oven to simulate actual heat history encountered on an industrial production level) for about 3 minutes allowing the material to cure to form a foam bun. A polyurethane foam article containing the odor control molecule of the present invention was thus produced.

Example 20, a branched PEI molecule (MW ~2000) capped with stearic acid, was prepared and evaluated for odor control in the following commercially available liquid and powder detergents:

Liquid Detergents: Purex®, Sun® Triple, Persil® Color & Gel, Persil®, All® Free & Clear, All® Plus, Kirkland™, Great Value™, Verve, Ariel, and Omo™ Sports;

Powder Detergents: Gain®), Omo™ Sports, Omo™ Perfeita, Surf® Excel, Rin, and Ghadi.

Example 20 was added to each detergent in amounts at both 0.5% and 1% by wt (resulting in 5 ppm and 10 ppm in wash water, respectively). Control samples for each detergent that did not contain the odor control molecule were also evaluated. All the samples containing the odor control molecule exhibited good performance (good odor control) with the Milk Test compared to the control samples.

Example 20 was also evaluated for use in Febreze® Fabric spray (commercially available from The Procter & Gamble Company of Cincinnati, Ohio). An amount of 1% by weight of the odor control molecule was added to Febreze® Fabric spray. Milk was sprayed on two carpet samples. For the first sample, only the Febreze® Fabric spray was applied. For the second sample, the formulation containing Febreze® Fabric spray and 1% by weight of the odor control molecule was applied. The sample treated with the odor control molecule did not exhibit any unpleasant odor after the Milk Test. In contrast, the sample not treated with the odor control molecule exhibited a very unpleasant odor.

In further testing, a solution containing 3% by weight of the odor control molecule of Example 20 and cyclodextrin (in a ratio of 1:3 of odor control molecule:cyclodextrin) was prepared. A control solution was prepared that contained only cyclodextrin. The solutions were applied independently to carpet samples. The carpet samples were then tested and evaluated using the Milk Test. The carpet samples treated with odor active molecule and cyclodextrin showed better odor control than the control samples treated only with cyclodextrin only.

Additional formulations were prepared that contained the odor control molecule of Example 20 and an anti-oxidant molecule in a 1:1 ratio by weight. Polyester fabric pieces were washed using the AATCC detergent containing the formulation having concentrations at 5 ppm and 10 ppm in wash water. The polyester fabric samples were then tested and evaluated using the Milk Test for both concentrations. Polyester fabric samples treated with anti-oxidant and the odor control molecule (in 1:1 ratio) showed better odor control than the control samples treated only with detergent containing the anti-oxidant molecule.

Further evaluation of the odor control molecule of the present invention was conducted. Samples were evaluated for odor and mildew growth using a Damp Towel Test:

Damp Towel Test: For mildew or musty smell test, 100% cotton white towels were soiled and then washed using AATCC detergent containing 0.5% by weight of the odor control molecule of Example 20. Control samples were also washed using the same detergent without Example 20 added to it (control samples). The towels were then partially dried (to approximately ~75% dry). The towels were subsequently kept in plastic bags for 5 days. The control damp towels (no odor control molecule included in detergent) developed a bad smell with some blackish gray patches visibly present on the towels. In contrast, the samples washed with AATCC detergent containing the odor control molecule did not show any bad smell and no visual change was observed on the white towels.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:

1. A process for controlling odor on a textile substrate comprising the steps of:
   (a) Providing a textile substrate, and
   (b) Applying to or depositing on the textile substrate a polyethyleneimine compound comprising a plurality of amine groups, each amine group comprising a nitrogen atom, wherein:
      i. at least one amine group comprises a nitrogen atom directly bonded to a functional group selected from the group consisting of alkanoyl groups, alkenoyl groups, aroyl groups, alkyl groups containing three or more carbon atoms, and aryl groups, and
      ii. at least one amine group comprises a nitrogen atom directly bonded to a halogen.

2. The process of claim 1, wherein step "b" is accomplished by adding the at least one polyethyleneimine compound to a laundry care composition and adding the laundry care composition to the textile substrate.

3. The process of claim 1, wherein step "b" is accomplished by adding the at least one polyethyleneimine compound to a floorcovering cleaning composition and adding the floorcovering cleaning composition to the textile substrate.

4. The process of claim 1, wherein the textile substrate is comprised of synthetic fiber, natural fiber, or mixtures thereof.

5. The process of claim 4, wherein synthetic fiber is polyester.

6. The process of claim 4, wherein natural fiber is cotton.

7. The process of claim 1, wherein the textile substrate is selected from the group consisting of articles of apparel, drapery, napery, residential upholstery, commercial upholstery, automotive upholstery, wall coverings, floorcovering articles, human bedding, pet bedding, outdoor fabric, and medical dressings.

8. The process of claim 1, wherein the process further includes performing at least one of agitating, rinsing, and drying the textile substrate.

9. The process of claim 1, wherein the polyethyleneimine compound further contains at least one polyalkyleneoxy chain.

10. The process of claim 9, wherein the at least one polyalkyleneoxy chain is a polymeric epoxide.

11. The process of claim 10, wherein the polymeric epoxide is selected from the group consisting of polyethylene oxides; polypropylene oxides; polybutylene oxides; oxetanes; tetrahydrafurans; copolymers of polyethylene oxides, polypropylene oxides and polybutylene oxides; and other copolymers including block copolymers, in which a majority of the polymeric substituent is polyethylene oxide, polypropylene oxide and/or polybutylene oxide.

12. The process of claim 1, wherein the halogen is selected from the group consisting of chlorine, bromine, fluorine, and iodine.

13. The process of claim 12, wherein the halogen is chlorine.

14. The process of claim 1, wherein the polyethyleneimine compound is linear or branched.

15. The process of claim 1, wherein the functional group is selected from the group consisting of $C_{10}$-$C_{26}$ alkanoyl groups, $C_{10}$-$C_{26}$ alkenoyl groups, aroyl groups, $C_{10}$-$C_{26}$ alkyl groups and aryl groups.

16. The process of claim 1, wherein the polyethyleneimine compound has a molecular weight in a range from 400 to 50,000.

17. An odor control molecule formed by reacting a polyethyleneimine molecule with stearic acid in the presence of an aqueous chlorine-containing solution.

18. The odor control molecule of claim 17, wherein the aqueous chlorine-containing solution is tap water.

19. The odor control molecule of claim 17, wherein aqueous chlorine-containing solution is deionized water having a chlorine-containing compound added thereto.

20. An odor control molecule comprising a halogenated polyethyleneimine, wherein odor control is achieved by proton transfer from at least one volatile carboxylic acid to the halogenated polyethyleneimine.

21. A process for controlling odor on a textile substrate comprising the steps of:
   (a) Providing a textile substrate, and
   (b) Treating the textile substrate with a compound formed by the reaction of polyethyleneimine with stearic acid in the presence of an aqueous chlorine-containing solution.

22. The process of claim 21, wherein the reaction results in the transfer of at least one proton from at least one volatile carboxylic acid to polyethyleneimine.

* * * * *